United States Patent
Ghosh et al.

(10) Patent No.: US 10,064,567 B2
(45) Date of Patent: Sep. 4, 2018

(54) SYSTEMS, METHODS, AND INTERFACES FOR IDENTIFYING OPTIMAL ELECTRICAL VECTORS

(71) Applicant: Medtronic, Inc., Minneapolis, MN (US)

(72) Inventors: Subham Ghosh, Blaine, MN (US); Jeffrey Gillberg, Coon Rapids, MN (US); Manfred Justen, Lino Lakes, MN (US); Eric Schilling, Ham Lake, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 188 days.

(21) Appl. No.: 14/227,919

(22) Filed: Mar. 27, 2014

(65) Prior Publication Data
US 2014/0323882 A1    Oct. 30, 2014

Related U.S. Application Data

(60) Provisional application No. 61/817,480, filed on Apr. 30, 2013, provisional application No. 61/913,784, filed on Dec. 9, 2013.

(51) Int. Cl.
*A61N 1/365* (2006.01)
*A61B 5/044* (2006.01)
(Continued)

(52) U.S. Cl.
CPC ............ *A61B 5/044* (2013.01); *A61B 5/0205* (2013.01); *A61B 5/4029* (2013.01); *A61N 1/365* (2013.01);
(Continued)

(58) Field of Classification Search
CPC ........................... A61N 1/3627; A61N 1/3684
See application file for complete search history.

(56) References Cited

U.S. PATENT DOCUMENTS 4,233,987 A   11/1980   Feingold
4,402,323 A    9/1983   White
(Continued)

FOREIGN PATENT DOCUMENTS

CN    1043621 A    7/1990
CN    1253761 A    5/2000
(Continued)

OTHER PUBLICATIONS

U.S. Appl. No. 14/173,288, filed Feb. 5, 2014, Sambelashvili.
(Continued)

*Primary Examiner* — Michael D Abreu
(74) *Attorney, Agent, or Firm* — Mueting, Raasch & Gebhardt, P.A.

(57) ABSTRACT

Systems, methods, and graphical user interfaces are described herein for identification of optimal electrical vectors for use in assisting a user in implantation of implantable electrodes to be used in cardiac therapy. Cardiac improvement information may be generated for each pacing configuration, and one or more pacing configuration may be selected based on the cardiac improvement information. Optimal electrical vectors using the selected pacing configurations may be identified using longevity information generated for each electrical vector. Electrodes may then be implanted for use in cardiac therapy to form the optimal electrical vector.

25 Claims, 16 Drawing Sheets

(51) Int. Cl.
*A61B 5/0205* (2006.01)
*A61B 5/00* (2006.01)
*A61N 1/368* (2006.01)
*A61N 1/37* (2006.01)
*A61N 1/372* (2006.01)

(52) U.S. Cl.
CPC ....... *A61N 1/3686* (2013.01); *A61N 1/36585* (2013.01); *A61N 1/371* (2013.01); *A61N 1/37247* (2013.01)

(56) References Cited

U.S. PATENT DOCUMENTS

| | | | |
|---|---|---|---|
| 4,428,378 | A | 1/1984 | Anderson et al. |
| 4,497,326 | A | 2/1985 | Curry |
| 4,566,456 | A | 1/1986 | Koning et al. |
| 4,593,702 | A | 6/1986 | Kepski |
| 4,674,511 | A | 6/1987 | Cartmell |
| 4,763,660 | A | 8/1988 | Kroll et al. |
| 4,777,955 | A | 10/1988 | Brayten et al. |
| 4,787,389 | A | 11/1988 | Tarjan |
| 4,979,507 | A * | 12/1990 | Heinz ..................... A61N 1/37 607/28 |
| 5,052,388 | A | 10/1991 | Sivula et al. |
| 5,054,496 | A | 10/1991 | Wen et al. |
| 5,311,873 | A | 5/1994 | Savard et al. |
| 5,331,960 | A | 7/1994 | Lavine |
| 5,334,220 | A | 8/1994 | Sholder |
| 5,443,492 | A | 8/1995 | Stokes et al. |
| 5,485,849 | A | 1/1996 | Panescu et al. |
| 5,514,163 | A | 5/1996 | Markowitz et al. |
| 5,552,645 | A | 9/1996 | Weng |
| 5,628,778 | A | 5/1997 | Kruse et al. |
| 5,671,752 | A | 9/1997 | Sinderby et al. |
| 5,683,429 | A | 11/1997 | Mehra |
| 5,683,432 | A | 11/1997 | Goedeke et al. |
| 5,687,737 | A | 11/1997 | Branham et al. |
| 5,810,740 | A | 9/1998 | Paisner |
| 5,876,336 | A | 3/1999 | Swanson et al. |
| 5,891,045 | A | 4/1999 | Albrecht et al. |
| 5,922,014 | A | 7/1999 | Warman et al. |
| 6,055,448 | A | 4/2000 | Anderson et al. |
| 6,128,535 | A | 10/2000 | Maarse et al. |
| 6,141,588 | A | 10/2000 | Cox et al. |
| 6,187,032 | B1 | 2/2001 | Ohyu et al. |
| 6,205,357 | B1 | 3/2001 | Ideker et al. |
| 6,226,542 | B1 | 5/2001 | Reisfeld |
| 6,236,883 | B1 | 5/2001 | Ciaccio et al. |
| 6,243,603 | B1 | 6/2001 | Ideker et al. |
| 6,246,898 | B1 | 6/2001 | Vesely et al. |
| 6,301,496 | B1 | 10/2001 | Reisfeld |
| 6,311,089 | B1 | 10/2001 | Mann et al. |
| 6,330,476 | B1 | 12/2001 | Ben-Haim et al. |
| 6,358,214 | B1 | 3/2002 | Tereschouk |
| 6,377,856 | B1 | 4/2002 | Carson |
| 6,381,493 | B1 | 4/2002 | Stadler et al. |
| 6,393,316 | B1 | 5/2002 | Gillberg et al. |
| 6,418,346 | B1 | 7/2002 | Nelson et al. |
| 6,442,433 | B1 | 8/2002 | Linberg |
| 6,456,867 | B2 | 9/2002 | Reisfeld |
| 6,473,638 | B2 | 10/2002 | Ferek-Petric |
| 6,480,745 | B2 | 11/2002 | Nelson et al. |
| 6,484,118 | B1 | 11/2002 | Govari |
| 6,507,756 | B1 | 1/2003 | Heynen et al. |
| 6,532,379 | B2 | 3/2003 | Stratbucker |
| 6,584,343 | B1 | 6/2003 | Ransbury et al. |
| 6,599,250 | B2 | 7/2003 | Webb et al. |
| 6,625,482 | B1 | 9/2003 | Panescu et al. |
| 6,640,136 | B1 | 10/2003 | Helland et al. |
| 6,650,927 | B1 | 11/2003 | Keidar |
| 6,766,189 | B2 | 7/2004 | Yu et al. |
| 6,772,004 | B2 | 8/2004 | Rudy |
| 6,804,555 | B2 | 10/2004 | Warkentin |
| 6,847,836 | B1 | 1/2005 | Sujdak |
| 6,856,830 | B2 | 2/2005 | He |
| 6,882,882 | B2 | 4/2005 | Struble et al. |
| 6,885,889 | B2 | 4/2005 | Chinchoy |
| 6,915,149 | B2 | 7/2005 | Ben-Haim |
| 6,968,237 | B2 | 11/2005 | Doan et al. |
| 6,975,900 | B2 | 12/2005 | Rudy et al. |
| 6,978,184 | B1 | 12/2005 | Marcus et al. |
| 6,980,675 | B2 | 12/2005 | Evron et al. |
| 7,016,719 | B2 | 3/2006 | Rudy et al. |
| 7,031,777 | B2 | 4/2006 | Hine et al. |
| 7,058,443 | B2 | 6/2006 | Struble |
| 7,062,315 | B2 | 6/2006 | Koyrakh et al. |
| 7,092,759 | B2 | 8/2006 | Nehls et al. |
| 7,142,922 | B2 | 11/2006 | Spinelli et al. |
| 7,184,835 | B2 | 2/2007 | Kramer et al. |
| 7,215,998 | B2 | 5/2007 | Wesselink et al. |
| 7,286,866 | B2 | 10/2007 | Okerlund et al. |
| 7,308,297 | B2 | 12/2007 | Reddy et al. |
| 7,308,299 | B2 | 12/2007 | Burrell et al. |
| 7,313,444 | B2 | 12/2007 | Pianca et al. |
| 7,321,677 | B2 | 1/2008 | Evron et al. |
| 7,346,381 | B2 | 3/2008 | Okerlund et al. |
| 7,398,116 | B2 | 7/2008 | Edwards |
| 7,426,412 | B1 | 9/2008 | Schecter |
| 7,454,248 | B2 | 11/2008 | Burrell et al. |
| 7,499,743 | B2 | 3/2009 | Vass et al. |
| 7,509,170 | B2 | 3/2009 | Zhang et al. |
| 7,565,190 | B2 | 7/2009 | Okerlund et al. |
| 7,587,074 | B2 | 9/2009 | Zarkh et al. |
| 7,599,730 | B2 | 10/2009 | Hunter et al. |
| 7,610,088 | B2 | 10/2009 | Chinchoy |
| 7,613,500 | B2 | 11/2009 | Vass et al. |
| 7,616,993 | B2 | 11/2009 | Müssig et al. |
| 7,664,550 | B2 | 2/2010 | Eick et al. |
| 7,684,863 | B2 | 3/2010 | Parikh et al. |
| 7,742,629 | B2 | 6/2010 | Zarkh et al. |
| 7,747,047 | B2 | 6/2010 | Okerlund et al. |
| 7,751,882 | B1 | 7/2010 | Helland et al. |
| 7,769,451 | B2 | 8/2010 | Yang et al. |
| 7,778,685 | B2 | 8/2010 | Evron et al. |
| 7,778,686 | B2 | 8/2010 | Vass et al. |
| 7,787,951 | B1 | 8/2010 | Min |
| 7,813,785 | B2 | 10/2010 | Okerlund et al. |
| 7,818,040 | B2 | 10/2010 | Spear et al. |
| 7,848,807 | B2 | 12/2010 | Wang |
| 7,860,580 | B2 | 12/2010 | Falk et al. |
| 7,894,889 | B2 | 2/2011 | Zhang |
| 7,912,544 | B1 | 3/2011 | Min et al. |
| 7,917,214 | B1 | 3/2011 | Gill et al. |
| 7,941,213 | B2 | 5/2011 | Markowitz et al. |
| 7,953,475 | B2 | 5/2011 | Harlev et al. |
| 7,953,482 | B2 | 5/2011 | Hess |
| 7,983,743 | B2 | 7/2011 | Rudy et al. |
| 7,996,063 | B2 | 8/2011 | Vass et al. |
| 7,996,070 | B2 | 8/2011 | van Dam et al. |
| 8,010,194 | B2 | 8/2011 | Muller |
| 8,019,402 | B1 | 9/2011 | Kryzpow et al. |
| 8,019,409 | B2 | 9/2011 | Rosenberg et al. |
| 8,032,229 | B2 | 10/2011 | Gerber et al. |
| 8,036,743 | B2 | 10/2011 | Savage et al. |
| 8,060,185 | B2 | 11/2011 | Hunter et al. |
| 8,150,513 | B2 | 4/2012 | Chinchoy |
| 8,160,700 | B1 | 4/2012 | Ryu et al. |
| 8,175,703 | B2 | 5/2012 | Dong et al. |
| 8,180,428 | B2 | 5/2012 | Kaiser et al. |
| 8,195,292 | B2 | 6/2012 | Rosenberg et al. |
| 8,213,693 | B1 | 7/2012 | Li |
| 8,214,041 | B2 | 7/2012 | Van Gelder et al. |
| 8,265,738 | B1 | 9/2012 | Min et al. |
| 8,285,377 | B2 | 10/2012 | Rosenberg et al. |
| 8,295,943 | B2 | 10/2012 | Eggen et al. |
| 8,326,419 | B2 | 12/2012 | Rosenberg et al. |
| 8,332,030 | B2 | 12/2012 | Hess et al. |
| 8,380,308 | B2 | 2/2013 | Rosenberg et al. |
| 8,401,616 | B2 | 3/2013 | Verard et al. |
| 8,478,388 | B2 | 7/2013 | Nguyen et al. |
| 8,527,051 | B1 | 9/2013 | Hedberg et al. |
| 8,583,230 | B2 | 11/2013 | Ryu et al. |
| 8,615,298 | B2 | 12/2013 | Ghosh et al. |
| 8,617,082 | B2 | 12/2013 | Zhang et al. |

(56) References Cited

U.S. PATENT DOCUMENTS

| | | |
|---|---|---|
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,972,228 B2 | 3/2015 | Ghosh et al. |
| 9,037,238 B2 | 5/2015 | Stadler et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1* | 3/2008 | Costello ............... A61B 5/1107 600/508 |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1* | 2/2009 | Brooke ............... A61N 1/36185 607/28 |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min et al. |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1* | 3/2011 | Rosenberg ............ A61N 1/3627 607/28 |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Ghosh et al. |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1 | 6/2013 | Bornzin et al. |
| 2013/0165983 A1 | 6/2013 | Ghosh et al. |
| 2013/0165988 A1 | 6/2013 | Ghosh |
| 2013/0261471 A1 | 10/2013 | Saha et al. |

(56) References Cited

U.S. PATENT DOCUMENTS

| | | |
|---|---|---|
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045849 A1 | 2/2015 | Ghosh et al. |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |
| 2015/0265840 A1 | 9/2015 | Ghosh et al. |
| 2016/0030747 A1 | 2/2016 | Thakur et al. |
| 2016/0030751 A1 | 2/2016 | Ghosh et al. |
| 2016/0045737 A1 | 2/2016 | Ghosh et al. |
| 2016/0045738 A1 | 2/2016 | Ghosh et al. |
| 2016/0045744 A1 | 2/2016 | Ghosh et al. |
| 2016/0184590 A1 | 6/2016 | Gosh |

FOREIGN PATENT DOCUMENTS

| | | |
|---|---|---|
| CN | 1878595 A | 12/2006 |
| CN | 101073502 A | 11/2007 |
| EP | 1 072 284 A2 | 1/2001 |
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 98/26712 A1 | 6/1998 |
| WO | WO 1999/006112 A1 | 2/1999 |
| WO | WO 00/45700 | 8/2000 |
| WO | WO 01/67950 A1 | 9/2001 |
| WO | WO 2003/070323 A1 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO/2012/151364 A1 | 11/2012 |
| WO | WO/2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | PCT/US2014/036153 | 4/2014 |
| WO | PCT/US2014/036163 | 4/2014 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

Biffi et al., "Occurrence of Phrenic Nerve Stimulation in Cardiac Resynchronization Therapy Patients: the Role of Left Ventricular Lead Type and Placement Site," *Europace*, 2013; 15:77-82.

Hayes et al., "Cardiac Resynchronization Therapy and the Relationship of Percent Biventricular Pacing to Symptoms and Survival," *Heart Rhythm*, Sep. 2011; 8(9):1469-1475.

Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.

Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.

International Search Report and Written Opinion dated May 3, 2012 for International Application No. PCT/US2012/036262; 9 pages.

International Search Report and Written Opinion dated May 3, 2012 for International Application No. PCT/US2012/036302; 9 pages.

International Search Report and Written Opinion dated Apr. 8, 2015, for International Application No. PCT/US2014/069070; 11 pages.

U.S. Appl. No. 13/916,353, filed Jun. 12, 2013, Ghosh.
U.S. Appl. No. 13/916,377, filed Jun. 12, 2013, Ghosh.
U.S. Appl. No. 13/952,043, filed Jul. 26, 2013, Ghosh.
U.S. Appl. No. 13/952,061, filed Jul. 26, 2013, Ghosh.
U.S. Appl. No. 14/190,508, filed Feb. 26, 2014.
U.S. Appl. No. 14/190,578, filed Feb. 26, 2014.
U.S. Appl. No. 14/220,733, filed Mar. 20, 2014, Ghosh et al.
U.S. Appl. No. 14/227,719, filed Mar. 27, 2014, Gillberg et al.
U.S. Appl. No. 14/227,919, filed Mar. 27, 2014, Ghosh et al.
U.S. Appl. No. 14/227,955, filed Mar. 27, 2014, Ghosh et al.
U.S. Appl. No. 14/227,962, filed Mar. 27, 2014, Ghosh et al.
U.S. Appl. No. 14/228,009, filed Mar. 27, 2014, Gillberg et al.
U.S. Appl. No. 14/228,024, filed Mar. 27, 2014, Ghosh et al.
U.S. Appl. No. 14/228,038, filed Mar. 27, 2014, Ghosh et al.

International Search Report and Written Opinion for PCT/US2014/036262, dated May 3, 2012; 9 pg.

International Search Report and Written Opinion for PCT/US2014/036302, dated May 3, 2012; 9 pg.

"CardioGuide System Enables Real-Time Navigation of Left Ventricular Leads During Medtronic CRT Implants," Press Release, Apr. 9, 2013, Medtronic, Inc., 2 pgs.

Czerwinska et al., "Method of Segmentation of Thorax Organs Images Applied to Modeling the Cardiac Electrical Field," *Engineering in Medicine and Biology Society*, Proceedings of the 22$^{nd}$ Annual International Conference of the IEEE, vol. 1, 23, Jul. 23, 2000.; pp. 402-405.

(56) References Cited

OTHER PUBLICATIONS

Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.
Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.
Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.
Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.
"Heart Failure Management" datasheet [online]. Medtronic, Minneapolis, Minnesota, [Last updated on Jun. 3, 2013].Retrieved from the Internet: www.medtronic.com; 9 pages.
Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.
Kornreich, "Body Surface Potential Mapping of ST Segment Changes in Acute Myocardial Infarction," *Circulation*, 1993; 87: 773-782.
Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.
Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.
Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.
Steinhaus BM., "Estimating cardiac transmembrane activation and recovery times from unipolar and bipolar extracellular electrograms : a simulation study," Circulation Research, 1989, 64:449-462.
Sweeney et al., "Analysis of Ventricular Activation Using Surface Electrocardiography to Predict Left Ventricular Reverse Volumetric Remoldeling During Cardiac Resynchronization Therapy," *Circulation*, Feb. 9, 2010; 121(5):626-34. Available online Jan. 25, 2010.
Turner et al, "Electrical and Mechanical Components of Dyssynchrony in Heart Failure Patients with Normal QRS Duration and Left Bundle-Branch Block," *Circulation* 2004; 109: 2544-2549.
Van Deursen et al., "Vectorcardiography as a Tool for Wasy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.
Varma et al., "Placebo CRT," *Journal of Cardiovascular Electrophysiology*, vol. 19, Aug. 2008; p. 878.
Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.

International Search Report and the Written Opinion of the International Searching Authority, dated Aug. 6, 2014, International Application No. PCT/US2014/036153, filed Apr. 30, 2014 (14 pgs).
International Search Report and Written Opinion for PCT/US2014/0247583, dated Nov. 4, 2014; 7 pages.
International Search Report and Written Opinion dated Nov. 12, 2014 for International Application No. PCT/US2014/047971; 7 pages.
International Search Report and Written Opinion dated Nov. 12, 2014 for International Application No. PCT/US2014/048120; 7 pages.
Cuculich et al., "The Electrophysiological Cardiac Ventricular Substrate in Patients After Myocardial Infarction," *J. Am. Coll. Cardiol.*, 2011; 58:1893-1902.
Dawoud et al., "Inverse Electrocardiographic Imaging to Assess Electrical Dyssynchrony in Cardiac Resynchronization Therapy Patients," *Computing in Cardiology*, 2012; 39:993-996.
Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.
Medtronic Vitatron Carelink Encore® Programmer Model 29901 Reference Manual, 2013, Medtronic, Inc., Minneapolis, MN.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" *Circulation*, 2013; 128: 2407-2418.
Strik et al., "Electrical and Mechanical Ventricular Activation During Left Bundle Branch Block and Resynchronization," *J. of Cardiovasc. Trans. Res.*, 2012; 5:117-126.
International Search Report and Written Opinion dated Jun. 11, 2015 for International Application No. PCT/US2015/021442; 13 pages.
International Search Report and Written Opinion dated Mar. 9, 2015, for International Application No. PCT/US2014/069214.
International Search Report and Written Opinion dated Mar. 17, 2015, for International Application No. PCT/US2014/069192.
International Search Report and Written Opinion dated Mar. 16, 2015, for International Application No. PCT/US2014/069182.
International Search Report / Written Opinion, dated Nov. 7, 2014; Patent Application No. PCT/US2014/036163, filed Apr. 30, 2014; 12 pages.
International Search Report / Written Opinion, dated Oct. 28, 2014; Patent Application No. PCT/US2014/041928, filed Jun. 11, 2014; 15 pages.
International Search Report / Written Opinion, dated Oct. 24, 2014; Patent Application No. PCT/US2014/041929, filed Jun. 11, 2014; 15 pages.
Miri et al., "Applicability of body surface potential map in computerized optimization of biventricular pacing," *Annals of Biomedical Engineering*, vol. 38, No. 3, Mar. 2010, pp. 865-875.
Miri et al., "Comparison of the electrophysiologically based optimization methods with different pacing parameters in patient undergoing resynchronization treatment," *30th Annual International IEEE EMBS Conference*, Aug. 2008, pp. 1741-1744.
Miri et al., "Computerized Optimization of Biventricular Pacing Using Body Surface Potential Map," *31st Annual International Conference of the IEEE EMBS*, Sep. 2009, pp. 2815-2818.
Miri et al., "Efficiency of Timing Delays and Electrode Positions in Optimization of Biventricular Pacing: A Simulation Study," *IEEE Transactions on Biomedical Engineering*, Nov. 2009, pp. 2573-2582.
Svendsen et al., "Computational Models of Cardiac Electrical Activation," Chapter 5, Computational Nov. 2010, pp. 73-88.
Wang et al., "Application of the Method of Fundamental Solutions to Potential-based Inverse Electrocardiography," *Annals of Biomedical Engineering*, Aug. 2006, pp. 1272-1288.
Botker MD, PhD., et al., "Electromechanical Mapping for Detection of Myocardial Viability in Patients with ischemia Cardiomyopathy," Circulation, Mar. 2001; vol. 103, No. 12, pp. 1631-1637.

(56) References Cited

OTHER PUBLICATIONS

Fung et al., Chapter 20, Optimization of Cardiac Resynchronization Therapy, Cardiac Resynchronization Therapy, Second Edition, Copyright 2008, Blackwell Publishing Ltd., pp. 356-373.
Hopenfeld et al., "The Effect of Conductivity on ST-Segment Epicardial Potentials Arising from Subendocardial Ischemia," Annals of Biomedical Eng., Jun. 2005; vol. 33, No. 6, pp. 751-763.
Nash et al., "An Experimental-Computational Framework for Validating in-vivo ECG Inverse Algorithms," International Journal of Bioelectromagnetism, vol. 2, No. 2, Dec. 31, 2000, 9 pp.
Sweeney et al., QRS Fusion Complex Analysis Using Wave Interference to Predict Reverse Remodeling During Cardiac Resynchronization Therapy, heart Rhythm, 2014, 11:806-813.
Wellens, MD et al., "The Electrocardiogram 102 Years After Einthoven," Circulation, Feb. 2004; vol. 109, No. 5, pp. 562-564.

\* cited by examiner

| Pacing Vector | Relative Longevity | Phrenic Nerve Stim present |
|---|---|---|
| LV2-RV Coil | 3 months less | Absent |
| LV2-LV1 | 6 months less | Absent |
| LV2-LV3 | Maximum | Absent |
| LV2-LV4 | Maximum | Present |
| LV3-RVCoil | 5 months less | Absent |
| LV3-LV1 | 4 months less | Absent |
| LV3-LV2 | 3 months less | Absent |
| LV3-LV4 | 1 year less | Present |

FIG. 10

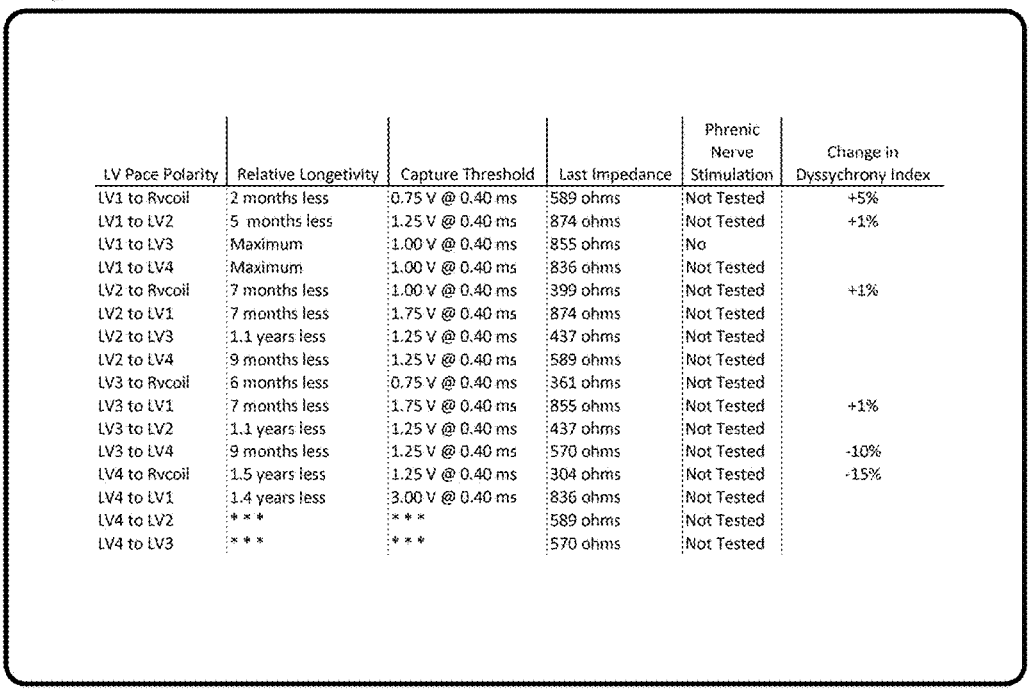

| LV Pace Polarity | Relative Longetivity | Capture Threshold | Last Impedance | Phrenic Nerve Stimulation | Change in Dyssychrony Index |
|---|---|---|---|---|---|
| LV1 to Rvcoil | 2 months less | 0.75 V @ 0.40 ms | 589 ohms | Not Tested | +5% |
| LV1 to LV2 | 5 months less | 1.25 V @ 0.40 ms | 874 ohms | Not Tested | +1% |
| LV1 to LV3 | Maximum | 1.00 V @ 0.40 ms | 855 ohms | No | |
| LV1 to LV4 | Maximum | 1.00 V @ 0.40 ms | 836 ohms | Not Tested | |
| LV2 to Rvcoil | 7 months less | 1.00 V @ 0.40 ms | 399 ohms | Not Tested | +1% |
| LV2 to LV1 | 7 months less | 1.75 V @ 0.40 ms | 874 ohms | Not Tested | |
| LV2 to LV3 | 1.1 years less | 1.25 V @ 0.40 ms | 437 ohms | Not Tested | |
| LV2 to LV4 | 9 months less | 1.25 V @ 0.40 ms | 589 ohms | Not Tested | |
| LV3 to Rvcoil | 6 months less | 0.75 V @ 0.40 ms | 361 ohms | Not Tested | |
| LV3 to LV1 | 7 months less | 1.75 V @ 0.40 ms | 855 ohms | Not Tested | +1% |
| LV3 to LV2 | 1.1 years less | 1.25 V @ 0.40 ms | 437 ohms | Not Tested | |
| LV3 to LV4 | 9 months less | 1.25 V @ 0.40 ms | 570 ohms | Not Tested | -10% |
| LV4 to Rvcoil | 1.5 years less | 1.25 V @ 0.40 ms | 304 ohms | Not Tested | -15% |
| LV4 to LV1 | 1.4 years less | 3.00 V @ 0.40 ms | 836 ohms | Not Tested | |
| LV4 to LV2 | * * * | * * * | 589 ohms | Not Tested | |
| LV4 to LV3 | * * * | * * * | 570 ohms | Not Tested | |

SYSTEMS, METHODS, AND INTERFACES FOR IDENTIFYING OPTIMAL ELECTRICAL VECTORS

CROSS-REFERENCE TO RELATED APPLICATIONS

This application claims the benefit of U.S. Provisional Patent Application 61/913,784 entitled "Systems, Methods, and Interfaces for Identifying Optimal Electrical Vectors" and filed on Dec. 9, 2013 and U.S. Provisional Patent Application 61/817,480 entitled "Identifying Optimal Electrical Vectors" and filed on Apr. 30, 2013, each of which is incorporated herein by reference in its entirety.

BACKGROUND

The disclosure herein relates to systems, methods, and interfaces for identifying optimal electrical vectors used to deliver therapy to tissue and/or sense signals from tissue. The identified vectors may be used in systems, methods, and interfaces for navigating an implantable electrode to a region of a patient's heart for cardiac therapy.

Electrodes may be used in various systems, apparatus, and methods for medical treatment of a patient. More specifically, electrodes may be located adjacent, or in contact, with tissue (e.g., skin, cardiac tissue, etc.) of a patient to deliver therapy to the tissue of the patient and/or sense signals from the tissue of the patient. Some electrodes may be more effective at delivering therapy than others (e.g., due to location, contact, etc.). Additionally, some of the more effective electrodes may form more effective or optimal electrical vectors for pacing than others.

SUMMARY

The exemplary systems, methods, and interfaces described herein may be configured to select one or more electrodes and/or pacing configurations based on cardiac improvement information (e.g., indicative of improvement in cardiac function) and identify one or more optimal electrical vectors that use the selected electrodes based on at least longevity information.

One exemplary system for identifying one or more optimal electrical vectors may include electrode apparatus and control apparatus. The electrode apparatus may include a plurality of electrodes (e.g., configured to pace at least one ventricle, coupled to at least one lead, etc.) configured to be located proximate tissue of a patient for pacing. The control apparatus may be coupled to the electrode apparatus and may be configured to deliver pacing therapy to the patient using each pacing configuration of a plurality of different pacing configurations, where each pacing configuration uses one or more electrodes of the plurality of electrodes to deliver electrical pacing stimulation, and to generate cardiac improvement information for each pacing configuration, where the cardiac improvement information is representative of a change in mechanical and/or electrical cardiac functionality resulting from pacing delivered using each pacing configuration. In at least one embodiment, a common anode may be used when delivering pacing therapy using each pacing configuration of the plurality of different pacing configurations to be used to generate cardiac improvement information. The cardiac improvement information may be representative of a change in mechanical and/or electrical cardiac functionality resulting from pacing delivered using each pacing configuration. The control apparatus may be further configured to select one or more pacing configurations of the plurality of different pacing configurations based on the cardiac improvement information, where each of the one or more selected pacing configurations are usable with one or more other electrodes to define a plurality of electrical vectors. The control apparatus may be further configured to generate longevity information for each electrical vector of the plurality of electrical vectors and identify one or more optimal electrical vectors of the plurality of electrical vectors based on the longevity information.

One exemplary method for identifying one or more optimal electrical vectors may include delivering pacing therapy using each pacing configuration of a plurality of different pacing configurations (e.g., configured to pace at least one ventricle, coupled to at least one lead, etc.), where each pacing configuration uses one or more electrodes of a plurality of electrodes to deliver electrical pacing stimulation, and generating cardiac improvement information for each pacing configuration, where the cardiac improvement information may be representative of a change in mechanical and/or electrical cardiac functionality resulting from pacing delivered using each pacing configuration. In at least one embodiment, a common anode may be used when delivering pacing therapy using each pacing configuration of the plurality of different pacing configurations to be used to generate cardiac improvement information. The exemplary method may further include selecting one or more pacing configurations of the plurality of different pacing configurations based on the cardiac improvement information, where each of the one or more selected pacing configurations are usable with one or more other electrodes to define a plurality of electrical vectors. The exemplary method may further include generating longevity information for each electrical vector of the plurality of electrical vectors and identifying one or more optimal electrical vectors of the plurality of electrical vectors based on the longevity information.

Another exemplary system for assisting a user in implantation of an implantable electrode for cardiac therapy may include means for deliver pacing therapy using each pacing configuration of a plurality of different pacing configurations and computing means for generating cardiac improvement information for each pacing configuration (e.g., the cardiac improvement information is representative of a change in mechanical and/or electrical cardiac functionality) and for selecting one or more pacing configurations of the plurality of different pacing configurations based on the cardiac improvement information. Each of the one or more selected pacing configurations may be usable with one or more other electrodes to define a plurality of electrical vectors. The computing means may further be for generating longevity information for each electrical vector of the plurality of electrical vectors and for identifying one or more optimal electrical vectors of the plurality of electrical vectors based on the longevity information.

An exemplary system for use in cardiac therapy may include electrode apparatus (e.g., a plurality of electrodes configured to be located proximate tissue of a patient for pacing), display apparatus (e.g., including a graphical user interface configured to present information for use in assisting a user in at least one of assessing a patient's cardiac health, evaluating and adjusting cardiac therapy delivered to a patient, and navigating at least one implantable electrode to a region of the patient's heart, etc.), and computing apparatus coupled to the electrode apparatus and display apparatus. The computing apparatus may be configured to deliver pacing therapy to the patient using each pacing configuration of a plurality of different pacing configurations (e.g., each pacing configuration uses one or more electrodes of the plurality of electrodes to deliver electrical pacing stimulation), generate cardiac improvement information for each pacing configuration (e.g., the cardiac improvement information is representative of a change in mechanical and/or electrical cardiac functionality resulting from pacing delivered using each pacing configuration), select one or more pacing configurations of the plurality of different pacing configurations based on the cardiac improvement information, where each of the one or more selected pacing configurations are usable with one or more other electrodes to define a plurality of electrical vectors, identify one or more optimal electrical vectors of the plurality of electrical vectors based on the longevity information, and display on the graphical user interface information for use in assisting a user in at least one of assessing a patient's cardiac health, evaluating and adjusting cardiac therapy delivered to a patient, and navigating at least one implantable electrode to a region of the patient's heart, wherein the information comprises the identified one or more optimal electrical vectors.

An exemplary method for use in cardiac therapy may include delivering pacing therapy using each pacing configuration of a plurality of different pacing configurations (e.g., configured to pace at least one ventricle, coupled to at least one lead, etc.), where each pacing configuration uses one or more electrodes of a plurality of electrodes to deliver electrical pacing stimulation, and generating cardiac improvement information for each pacing configuration, where the cardiac improvement information may be representative of a change in mechanical and/or electrical cardiac functionality resulting from pacing delivered using each pacing configuration, and selecting one or more pacing configurations of the plurality of different pacing configurations based on the cardiac improvement information, where each of the one or more selected pacing configurations are usable with one or more other electrodes to define a plurality of electrical vectors. The exemplary method may further include generating longevity information for each electrical vector of the plurality of electrical vectors, identifying one or more optimal electrical vectors of the plurality of electrical vectors based on the longevity information, displaying on a graphical user interface information for use in assisting a user in at least one of assessing a patient's cardiac health, evaluating and adjusting cardiac therapy delivered to a patient, and navigating at least one implantable electrode to a region of the patient's heart, wherein the information comprises the identified one or more optimal electrical vectors of the plurality of electrical vectors.

Another exemplary system for use in cardiac therapy may include means for deliver pacing therapy using each pacing configuration of a plurality of different pacing configurations and computing means for generating cardiac improvement information for each pacing configuration (e.g., the cardiac improvement information is representative of a change in mechanical and/or electrical cardiac functionality) and for selecting one or more pacing configurations of the plurality of different pacing configurations based on the cardiac improvement information. Each of the one or more selected pacing configurations may be usable with one or more other electrodes to define a plurality of electrical vectors. The computing means may further be for generating longevity information for each electrical vector of the plurality of electrical vectors and for identifying one or more optimal electrical vectors of the plurality of electrical vectors based on the longevity information. The exemplary system may further include display means for providing a graphical user interface displaying information for use in assisting a user in at least one of assessing a patient's cardiac health, evaluating and adjusting cardiac therapy delivered to a patient, and navigating at least one implantable electrode to a region of the patient's heart, wherein the information comprises the identified one or more optimal electrical vectors of the plurality of electrical vectors.

In one or more exemplary embodiments, the graphical user interface may include the identified one or more optimal electrical vectors on the at least a portion of anatomy of the patient's heart. In one or more exemplary embodiments, one or more candidate regions proximate the patient's heart for implantation of an implantable electrode based on the identified one or more optimal electrical vectors may be determined (e.g., using computing means, computing apparatus, display means, display apparatus, etc.) and the one or more candidate site regions may be identified on the graphical user interface on the at least a portion of anatomy of the patient's heart for implantation of the implantable electrode. In at least one embodiment, the information displayed, on the graphical user interface, may include at least a portion of anatomy of the patient's heart (e.g., at least a portion of the blood vessel anatomy of the patient's heart, at least a portion of the coronary sinus, etc.).

In one or more embodiments, generating cardiac improvement information for each electrode may include generating dyssynchrony information, or measures of electrical heterogeneity, for each pacing configuration by monitoring heart function using a plurality of surface electrodes during pacing and/or using cardiac imaging apparatus during pacing.

In one or more embodiments, the dyssynchrony information may include a dyssynchrony improvement value for each pacing configuration, and the dyssynchrony improvement value may be generated by comparing baseline dyssynchrony to paced dyssynchrony during pacing using each electrode.

In one or more embodiments, selecting one or more pacing configurations based on the cardiac improvement information may include defining a threshold value based on the dyssynchrony information and selecting one or more pacing configurations having a dyssynchrony improvement value greater than the threshold value. In at least one embodiment, the threshold value may be set to a maximum generated dyssynchrony improvement value multiplied by a factor, where the factor is selected based on the maximum generated dyssynchrony improvement value.

In one or more embodiments, the control module may be further configured to execute or the method may further include delivering pacing therapy using at least one pacing configuration that uses two or more electrodes of the plurality of electrodes per cardiac cycle if the cardiac improvement information generated for each pacing configuration that uses one electrode of the plurality of electrodes does not meet a threshold criteria.

In one or more embodiments, generating longevity information for each electrical vector of the plurality of electrical vectors may include determining at least one of a capture threshold for each electrical vector and an impedance value for each electrical vector.

In one or more embodiments, the control module may be further configured to execute or the method may further include determining whether each electrical vector stimulates the phrenic nerve and identifying the one or more optimal electrical vectors of the plurality of electrical vectors based on an absence of phrenic nerve stimulation.

In one or more embodiments, identifying the one or more optimal electrical vectors of the plurality of electrical vectors based on the longevity information may include identifying the electrical vector having at least one of the greatest longevity, lowest capture threshold, and smallest impedance.

One exemplary system and/or method may involve automatically selecting an optimal pacing vector for a multipolar cardiac resynchronization therapy (CRT) lead (e.g., a left ventricular lead, a right ventricular lead, etc.). In at least one embodiment, an electrode may be automatically selected without ranking the electrodes. Once a determination is made that an electrode performs above a preselected threshold that relates to maximal improvement, the electrode may be selected. In at least one embodiment, the system and/or method may automatically weigh data related to dyssynchrony or rhythm improvement against battery longevity, capture threshold, and phrenic nerve stimulation. Based upon this data, the exemplary system and/or method may determine that equivalent electrodes exist. Electrodes may be deemed equivalent based upon certain criteria (e.g., relative improvement of cardiac dyssynchrony). Instead of re-evaluating all of the electrodes, the system and/or method may automatically eliminate certain electrodes and focus on the equivalent electrodes for any additional testing thereby reducing implant time.

After an LV lead has been placed at a target location, an exemplary method may automatically initiate a sequence of setting CRT pacing parameters from a programmer/analyzer, measure dyssynchrony, modify the CRT pacing parameters, measure dyssynchrony, and repeat until all desired configurations are measured. In at least one embodiment, the exemplary processes and/or methods may be directly integrated with an exemplary system, which could control the sequencing of changes to CRT pacing configurations, and an exemplary system (e.g., imaging system) could measure dyssynchrony (e.g., relative improvements in dyssynchrony from a given electrode compared to a baseline rhythm). The system may be further configured to recognize the displayed pacing parameters via character recognition from the video output of the programmer/analyzer.

In at least one embodiment, a fully-automated application within an exemplary system may communicate a desired sequencing of changes to CRT pacing configurations to the programmer/analyzer (via Ethernet or wireless network).

In at least one embodiment, some of the pacing parameters may be manually modified using a programmer/analyzer. An exemplary system may measure dyssynchrony and recognize displayed pacing parameters via character recognition from the video output of the programmer/analyzer.

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIG. 9 is an exemplary graphical user interface depicting a table of longevity information for a plurality of electrode vectors.

FIG. 10 is an exemplary graphical user interface depicting a table of longevity information, phrenic nerve stimulation, and cardiac improvement information for a plurality of electrical vectors.

DETAILED DESCRIPTION OF EXEMPLARY EMBODIMENTS

Figure 1:
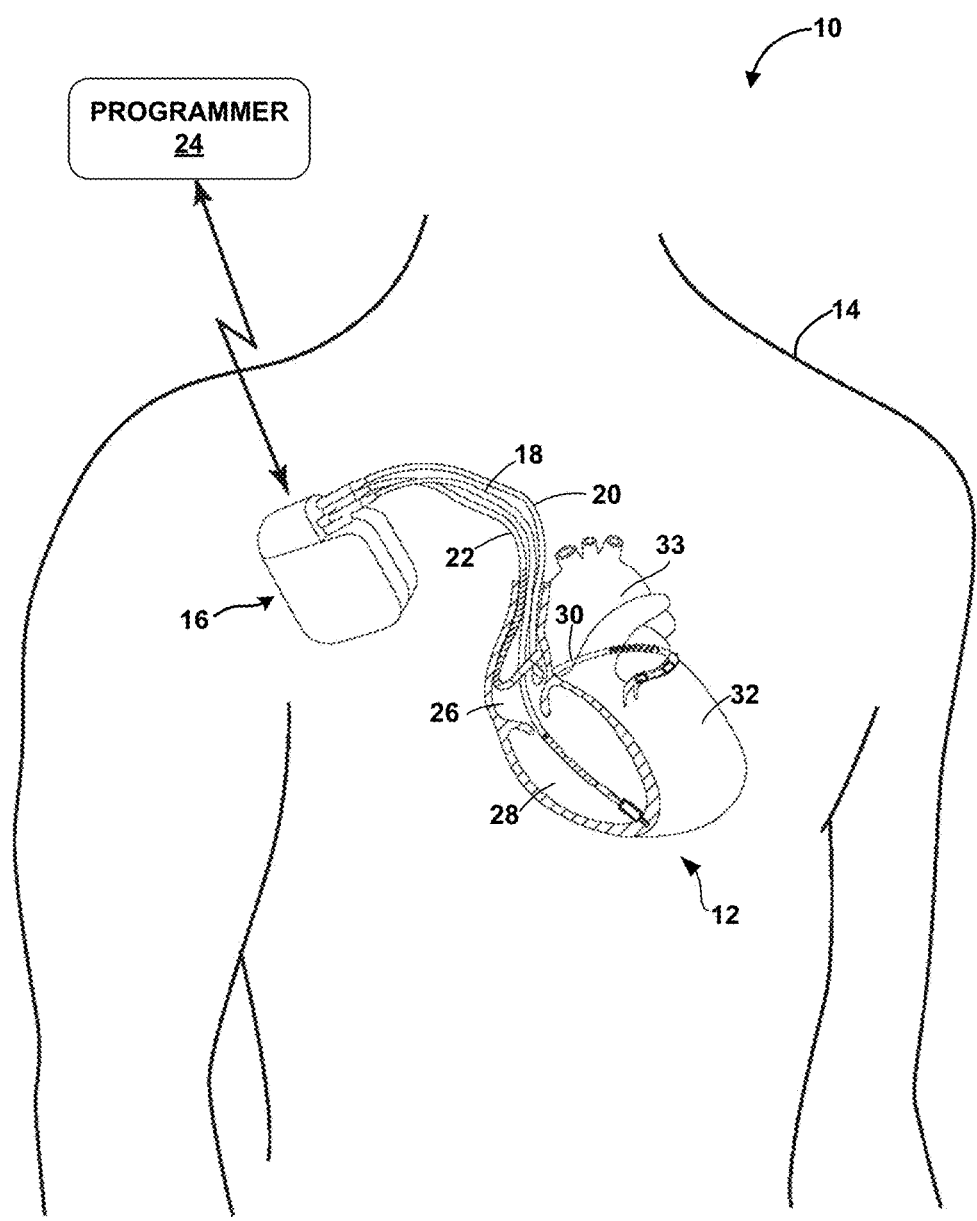
FIG. 1 is a diagram of an exemplary system including an exemplary implantable medical device (IMD).

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems, methods, and interfaces shall be described with reference to FIGS. 1-13. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

As described herein, various exemplary systems, methods, and interfaces may utilize electrodes configured to deliver therapy to tissue of a patient and/or sense one or more signals from the tissue of the patient. For example, electrodes may be included as part of an implantable medical device (IMD) and located on one or more leads configured to be located proximate one or more portions of a patient's heart.

The exemplary methods and processes described herein may be utilized and implemented by one or more (e.g., two or more, a plurality, etc.) systems, apparatus, and devices that include and/or are coupled to at least one electrode. For example, the exemplary methods and processes may be used by an exemplary therapy system 10 described herein with reference to FIGS. 1-3 and exemplary system 100 including a spatial electrode-array as described herein with reference to FIGS. 5A-5B. Although only therapy system 10 and sensing system 100 are described and depicted herein, it is to be understood that the exemplary methods and processes may be used by any system including computing apparatus capable of analyzing signals from one or more electrodes. The computing apparatus, for example, may be located in an external computer or programmer, may be located in an IMD, or may be located on a server attached to a network.

FIG. 1 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22 and/or a programmer 24. The IMD 16 may be, e.g., an implantable pacemaker, cardioverter, and/or defibrillator, that provides electrical signals to the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. The IMD 16 may be configured to determine or identify effective electrodes located on the leads 18, 20, 22 using the exemplary methods and processes described herein. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., AV delay and other various timings, pulse width, amplitude, voltage, burst length, etc. Further, the IMD 16 may be operable to use various electrode configurations to deliver pacing therapy, which may be unipolar, bipolar, quadripoloar, or further multipolar. For example, a multipolar lead may include several electrodes which can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

In some examples, a programmer 24, which may be a handheld computing device or a computer workstation, may be used by a user, such as a physician, technician, another clinician, and/or patient, to communicate with the IMD 16 (e.g., to program the IMD 16). For example, the user may interact with the programmer 24 to retrieve information concerning cardiac improvement information (e.g., dyssynchrony information, etc.) for one or more electrodes, longevity information (e.g., capture threshold information, impedance values, etc.) with respect to one or more electrical vectors, and/or whether one or more electrical vectors stimulate the phrenic nerve. Additionally, the user may interact with the programmer 24 to selected one or more optimal electrical vectors, e.g., for use in delivering therapy. Further, the user may interact with the programmer 24 to retrieve information concerning one or more detected or indicated faults associated within the IMD 16 and/or the pacing therapy delivered therewith. For instance, computing apparatus located in one or both of the IMD 16 and the programmer 24 may be configured to analyze or evaluate signals from one or more electrodes to selected one or more electrodes and identify one or more optimal electrical vectors. The IMD 16 and the programmer 24 may communicate via wireless communication using any techniques known in the art. Examples of communication techniques may include, e.g., low frequency or radiofrequency (RF) telemetry, but other techniques are also contemplated.

Figure 2A:
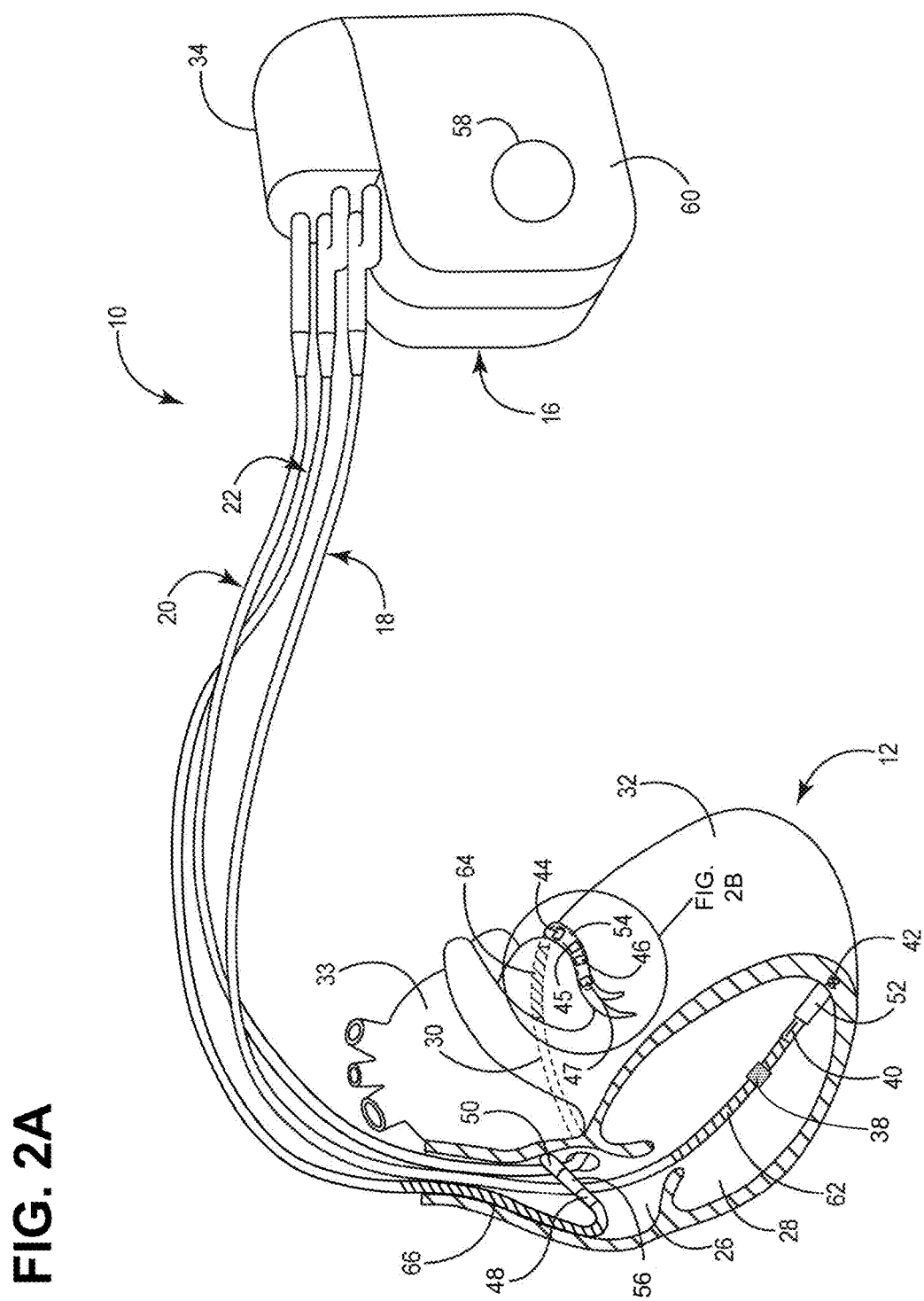
FIG. 2A is a diagram of the exemplary IMD of FIG. 1.

FIG. 2A is a conceptual diagram illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, the bipolar electrodes 44, 45, 46, 47 are located proximate to a distal end of the lead 20 and the bipolar electrodes 48, 50 are located proximate to a distal end of the lead 22.

The electrodes 40, 44, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22.

Additionally, electrodes 44, 45, 46 and 47 may have an electrode surface area of about 5.3 $mm^2$ to about 5.8 $mm^2$. Electrodes 44, 45, 46, and 47 may also referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The sensed electrical signals may be used to determine which the electrodes 40, 42, 44, 45, 46, 47, 48, 50 are the most effective in improving cardiac function. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 2A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48 and 50 may be used for unipolar sensing or pacing in combination with housing electrode 58. In other words, any of electrodes 40, 42, 44, 45, 46, 47, 48, 50, 58 may be used in combination to form a sensing vector, e.g., a sensing vector that may be used to evaluate and/or analyze the effectiveness of pacing therapy. It is generally understood by those skilled in the art that other electrodes can also be selected to define, or be used for, pacing and sensing vectors. Further, any of electrodes 40, 42, 44, 45, 46, 47, 48, 50, 58, which are not being used to deliver pacing therapy, may be used to sense electrical activity during pacing therapy.

As described in further detail with reference to FIGS. 3A-3B, the housing 60 may enclose a therapy delivery module that may include a stimulation generator for generating cardiac pacing pulses and defibrillation or cardioversion shocks, as well as a sensing module for monitoring the patient's heart rhythm. The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity (e.g., for use in determining electrode effectiveness, for use in analyzing pacing therapy effectiveness, etc.) and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58 forming a RV elongated coil, or defibrillation electrode-to-housing electrode vector).

Figure 2B:
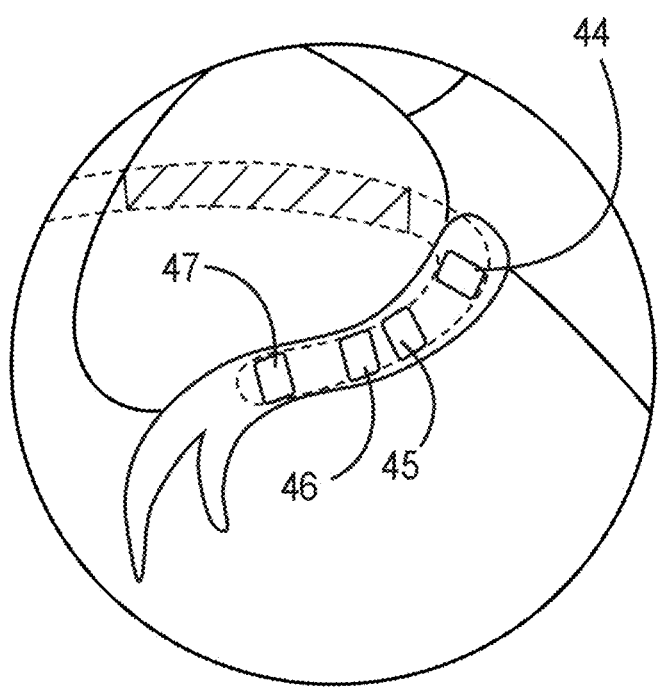
FIG. 2B is a diagram of an enlarged view of a distal end of the electrical lead disposed in the left ventricle of FIG. 2A.

The configuration of the exemplary therapy system 10 illustrated in FIGS. 1-2 is merely one example. In other examples, the therapy system may include epicardial leads and/or patch electrodes instead of or in addition to the transvenous leads 18, 20, 22 illustrated in FIG. 1. Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 1-2. Still further, other therapy systems may include a single lead that extends from the IMD 16 into the right atrium 26 or the right ventricle 28, or two leads that extend into a respective one of the right atrium 26 and the right ventricle 28.

Figure 3A:
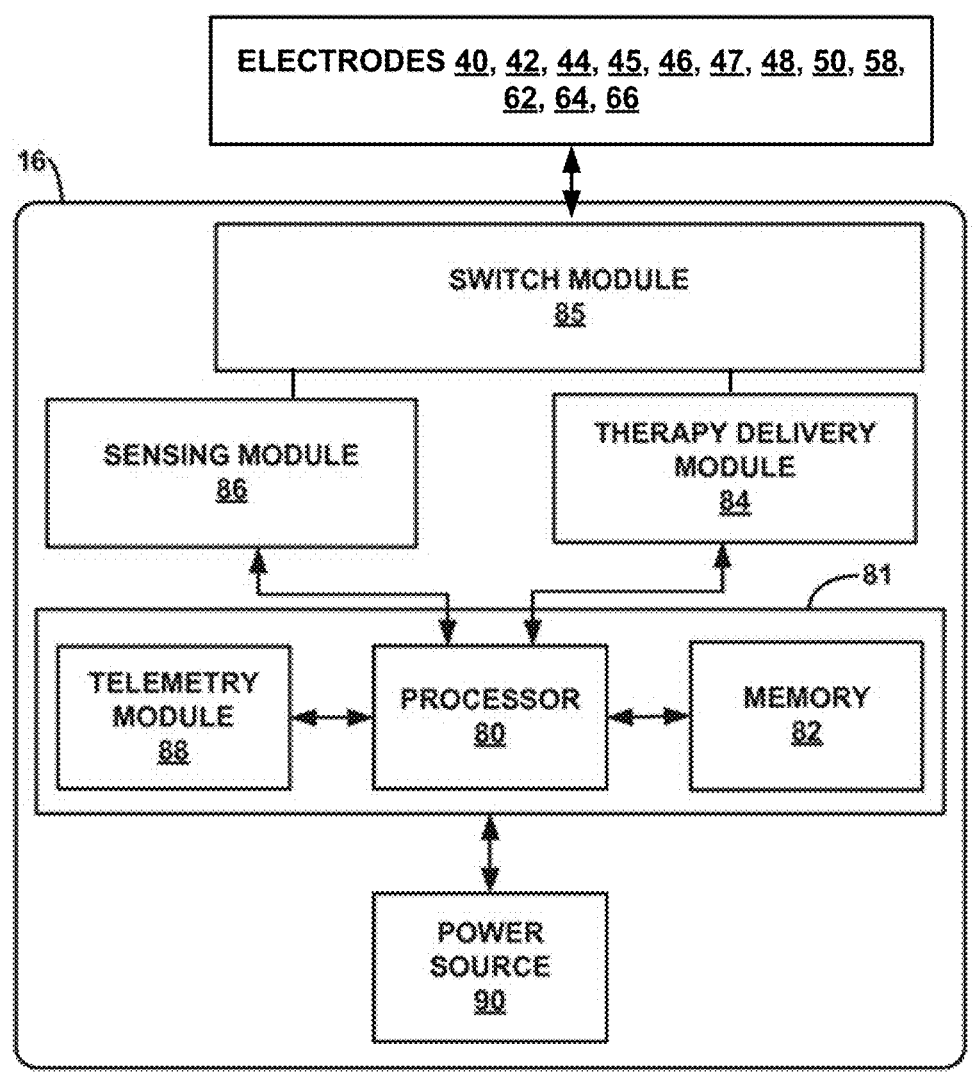
FIG. 3A is a block diagram of an exemplary IMD, e.g., the IMD of FIGS. 1-2.

FIG. 3A is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may be used to determine the effectiveness of the electrodes 40, 42, 44, 45, 46, 47, 48, 50, 58, 62, 64, 66 using the exemplary methods and/or processes described herein according to a selected one or more programs, which may be stored in the memory 82. Further, the control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., AV delays, pacing pulses with the amplitudes, pulse widths, frequency, or electrode polarities, etc., which may be specified by one or more selected therapy programs (e.g., AV delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, and 22, respectively, and/or tip electrodes 42 and 50 of leads 18 and 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to identify the effectiveness of each of the electrodes 40, 42, 44, 45, 46, 47, 48, 50, 58, 62, 64, 66 (e.g., by monitoring or measuring the signals for analysis by the control module 81, the programmer 24, etc.). Further, the ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may be also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit. The control module 81 (e.g., using the processor 80) may employ digital signal analysis techniques to characterize the digitized signals stored in memory 82 to analyze and/or classify one or more morphological waveforms of the EGM signals to determine pacing therapy effectiveness, etc. For example, the processor 80 may be configured to determine, or obtain, one more features of one or more sensed morphological waveforms within one of more electrical vectors of the patient's heart and store the one or more features within the memory 82 for use in comparing features, values, etc. of the waveforms to determine effectiveness of the electrodes.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as the programmer 24 as described herein with respect to FIG. 1. For example, under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 3B:
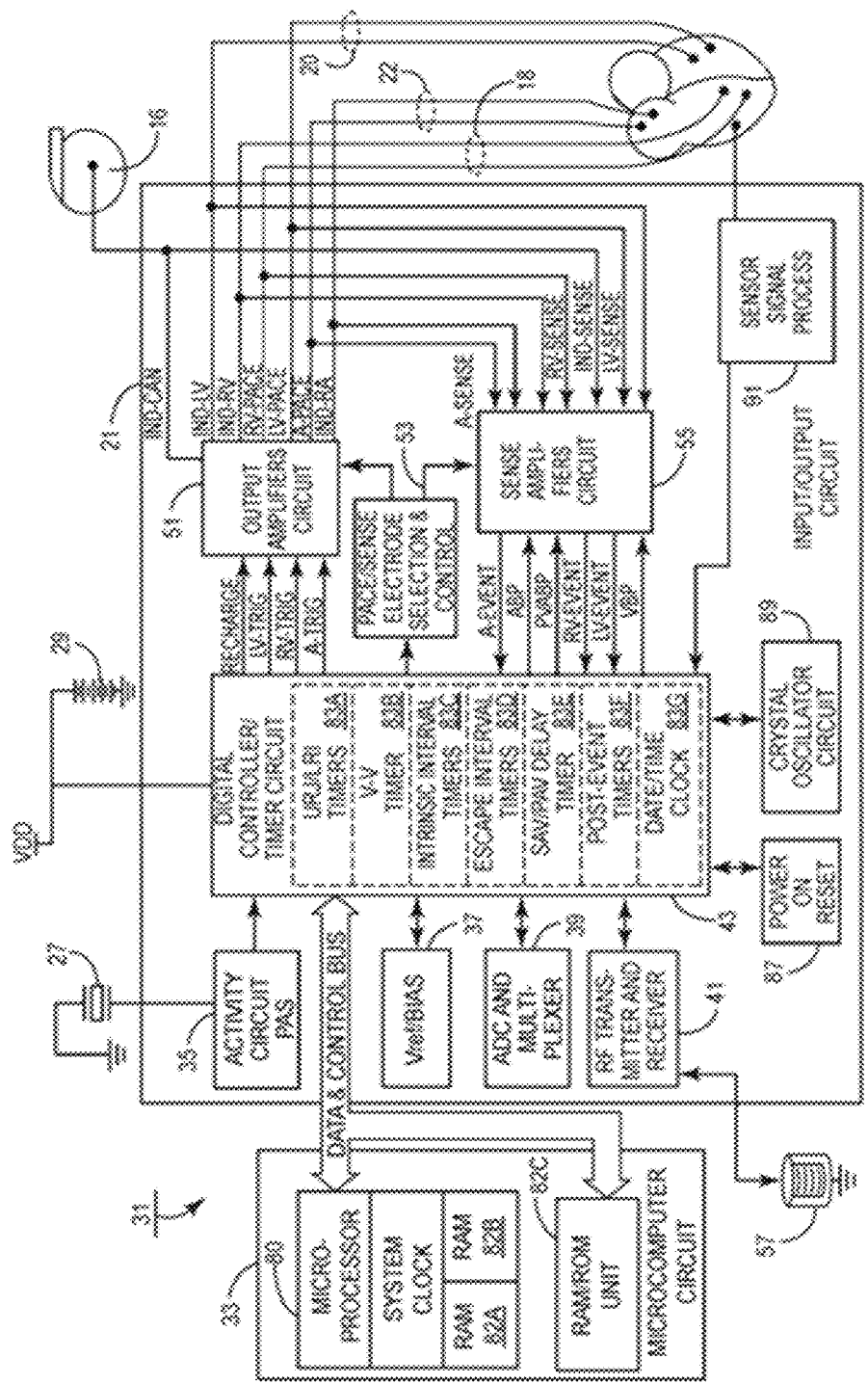
FIG. 3B is another block diagram of an exemplary IMD (e.g., an implantable pulse generator) circuitry and associated leads employed in the system of FIGS. 1-2 for providing three sensing channels and corresponding pacing channels.

FIG. 3B is another embodiment of a functional block diagram for IMD 16. FIG. 3B depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 83 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 83, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21, while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21, while analog to digital converter ADC and multiplexer circuit 39 digitizes analog signals and voltage to provide real time telemetry if a cardiac signals from sense amplifiers 55, for uplink transmission via RF transmitter and receiver circuit 41. Voltage reference and bias circuit 37, ADC and multiplexer 39, power-on-reset circuit 87 and crystal oscillator circuit 89 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer as is well known in the art and its output signal is processed and used as the RCP. Sensor 27 generates electrical signals in response to sensed physical activity that are processed by activity circuit 35 and provided to digital controller/timer circuit 83. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which is incorporated herein by reference in their entirety. Similarly, the exemplary systems, apparatus, and methods described herein may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and marker channel pulses indicating the occurrence of sensed and paced depolarizations in the atrium and ventricle, as are well known in the pacing art.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 83 and A-EVENT, RV-EVENT, and LV-EVENT signals generated by sense amplifiers circuit 55, among others. The specific values of the intervals and delays timed out by digital controller/timer circuit 83 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals and the energy delivered to each ventricle.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 83 operates under the general control of the microcomputer 33 to control timing and other functions within the pacing circuit 320 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp delay as determined using known methods) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F time out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, post-ventricular time periods, and post-atrial time periods that vary with the sensor based escape interval established in response to the RCP(s) and/or with the intrinsic atrial rate.

The output amplifiers circuit 51 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 83 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers corresponding to any of those presently employed in contemporary cardiac pacemakers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the atrial and ventricular sense amplifiers 55.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier, if provided, result in a LA-EVENT signal that is communicated to the digital controller/timer circuit 83. Ventricular depolarizations or R-waves in the RV-SENSE signal are sensed by a ventricular sense amplifier result in an RV-EVENT signal that is communicated to the digital controller/timer circuit 83. Similarly, ventricular depolarizations or R-waves in the LV-SENSE signal are sensed by a ventricular sense amplifier result in an LV-EVENT signal that is communicated to the digital controller/timer circuit 83. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

Figure 4:
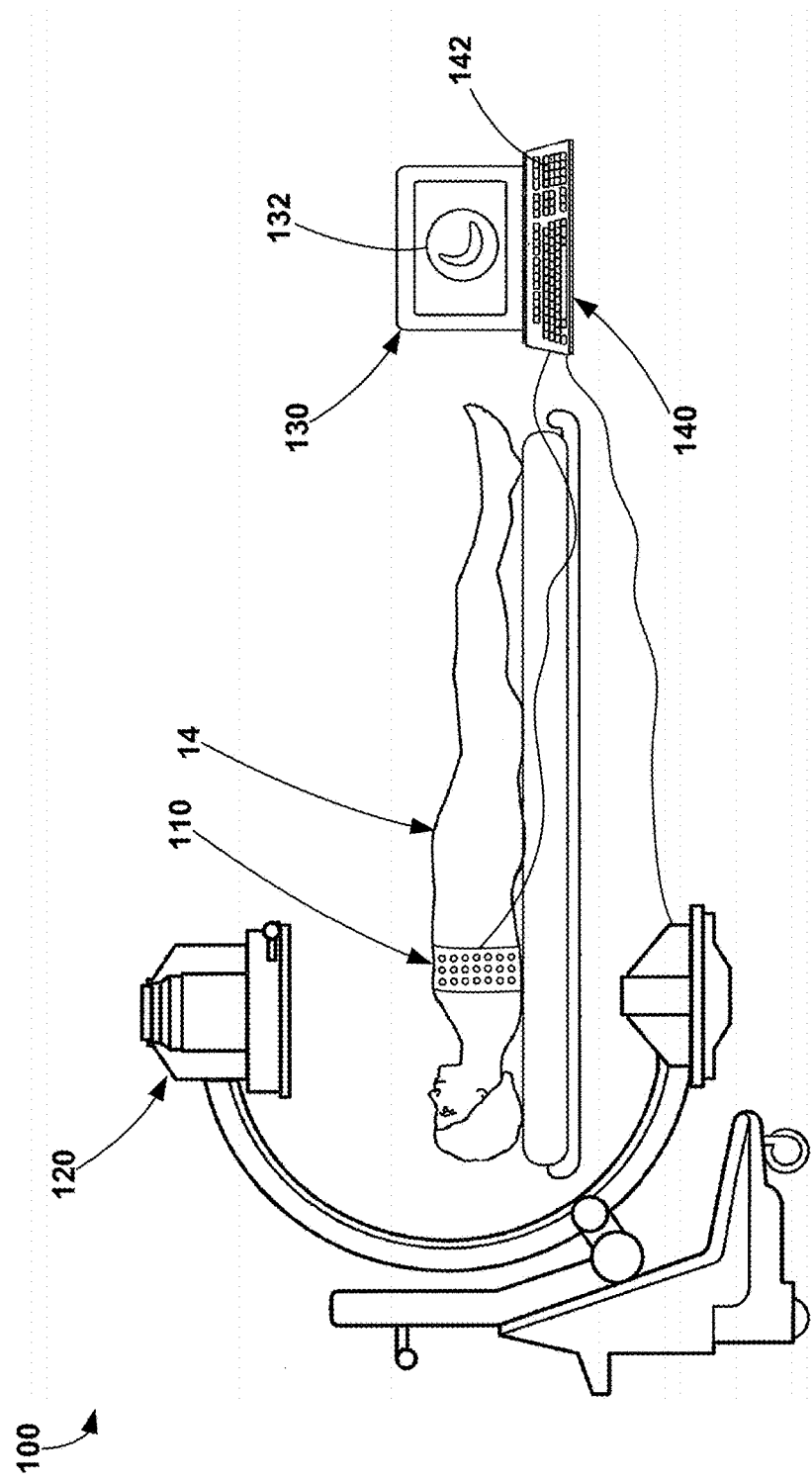
FIG. 4 is a diagram of an exemplary system including electrode apparatus, imaging apparatus, display apparatus, and computing apparatus.

As described herein, various exemplary systems, methods, and interfaces may be configured to use electrode apparatus including external electrodes, imaging apparatus, display apparatus, and computing apparatus to noninvasively assist a user (e.g., a physician) in selecting one or more locations (e.g., implantation site regions) proximate a patient's heart for one or more implantable electrodes and/or to navigate one or more implantable electrodes to the selected location(s). An exemplary system 100 including electrode apparatus 110, imaging apparatus 120, display apparatus 130, and computing apparatus 140 is depicted in FIG. 4.

The electrode apparatus 110 as shown includes a plurality of electrodes incorporated, or included within a band wrapped around the chest, or torso, of a patient 14. The electrode apparatus 110 is operatively coupled to the computing apparatus 140 (e.g., through one or more wired electrical connections, wirelessly, etc.) to provide electrical signals from each of the electrodes to the computing apparatus 140 for analysis. Exemplary electrode apparatus may be described in U.S. Provisional Patent Application entitled "Bioelectric Sensor Device and Methods" and filed on Dec. 9, 2013 and U.S. patent application entitled "Bioelectric Sensor Device and Methods" and filed on even date herewith, each of which is incorporated herein by reference in its entirety. Further, exemplary electrode apparatus 110 will be described in more detail in reference to FIGS. 5A-5B.

The imaging apparatus 120 may be any type of imaging apparatus configured to image, or provide images of, at least a portion of the patient in a non-invasive manner. For example, the imaging apparatus 120 may not use any components or parts that may be located within the patient to provide images of at least a portion of the patient except non-invasive tools such as contrast solution. It is to be understood that the exemplary systems, methods, and interfaces described herein may noninvasively assist a user (e.g., a physician) in selecting a location proximate a patient's heart for an implantable electrode, and after the exemplary systems, methods, and interfaces have provided noninvasive assistance, the exemplary systems, methods, and interfaces may then provide assistance to implant, or navigate, an implantable electrode into the patient, e.g., proximate the patient's heart.

For example, after the exemplary systems, methods, and interfaces have provided noninvasive assistance, the exemplary systems, methods, and interfaces may then provide image guided navigation that may be used to navigate leads including electrodes, leadless electrodes, wireless electrodes, catheters, etc., within the patient's body. Further, although the exemplary systems, methods, and interfaces are described herein with reference to a patient's heart, it is to be understood that the exemplary systems, methods, and interfaces may be applicable to any other portion of the patient's body.

The imaging apparatus 120 may be configured to capture, or take, x-ray images (e.g., two dimensional x-ray images, three dimensional x-ray images, etc.) of the patient 14. The imaging apparatus 120 may be operatively coupled (e.g., through one or more wired electrical connections, wirelessly, etc.) to the computing apparatus 140 such that the images captured by the imaging apparatus 120 may be transmitted to the computing apparatus 140. Further, the computing apparatus 140 may be configured to control the imaging apparatus 120 to, e.g., configure the imaging apparatus 120 to capture images, change one or more settings of the imaging apparatus 120, etc.

It will be recognized that while the imaging apparatus 120 as shown in FIG. 4 may be configured to capture x-ray images, any other alternative imaging modality may also be used by the exemplary systems, methods, and interfaces described herein. For example, the imaging apparatus 120 may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus 120 may be configured to capture a plurality of consecutive images (e.g., continuously) to provide video frame data. In other words, a plurality of images taken over time using the imaging apparatus 120 may provide motion picture data. Additionally, the images may also be obtained and displayed in two, three, or four dimensions. In more advanced forms, four-dimensional surface rendering of the heart or other regions of the body may also be achieved by incorporating heart data or other soft tissue data from an atlas map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data to be used to confidently reach target locations within the heart or other areas of interest.

The display apparatus 130 and the computing apparatus 140 may be configured to display and analyze data such as, e.g., surrogate electrical activation data, image data, mechanical motion data, etc. gathered, or collected, using the electrode apparatus 110 and the imaging apparatus 120 to noninvasively assist a user in location selection of an implantable electrode. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for driving a graphical user interface configured to noninvasively assist a user in location selection of an implantable electrode, etc.

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 to view and/or select one or more target or candidate locations of a portion of a patient's heart as further described herein.

Although as depicted the input apparatus 142 is a keyboard, it is to be understood that the input apparatus 142 may include any apparatus capable of providing input to the computing apparatus 140 to perform the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including graphical depictions of anatomy of a patient's heart, images of a patient's heart, graphical depictions of locations of one or more electrodes, graphical depictions of one or more target or candidate locations, alphanumeric representations of one or more values, graphical depictions or actual images of implanted electrodes and/or leads, etc. For example, the display apparatus 130 may include a liquid crystal display, an organic light-emitting diode screen, a touchscreen, a cathode ray tube display, etc.

The graphical user interfaces 132 displayed by the display apparatus 130 may include, or display, one or more regions used to display graphical depictions, to display images, to allow selection of one or more regions or areas of such graphical depictions and images, etc. As used herein, a "region" of a graphical user interface 132 may be defined as a portion of the graphical user interface 132 within which information may be displayed or functionality may be performed. Regions may exist within other regions, which may be displayed separately or simultaneously. For example, smaller regions may be located within larger regions, regions may be located side-by-side, etc. Additionally, as used herein, an "area" of a graphical user interface 132 may be defined as a portion of the graphical user interface 132 located with a region that is smaller than the region it is located within. Exemplary systems and interfaces may be described in U.S. Provisional Patent Application 61/913,743 entitled "Noninvasive Cardiac Therapy Evaluation" and filed on Dec. 9, 2013 and U.S. patent application entitled "Noninvasive Cardiac Therapy Evaluation" and filed on even date herewith, each of which is incorporated herein by reference in its entirety.

The processing programs or routines stored and/or executed by the computing apparatus 140 may include programs or routines for computational mathematics, matrix mathematics, decomposition algorithms, compression algorithms (e.g., data compression algorithms), calibration algorithms, image construction algorithms, signal processing algorithms (e.g., Fourier transforms, fast Fourier transforms, etc.), standardization algorithms, comparison algorithms, vector mathematics, or any other processing required to implement one or more exemplary methods and/or processes described herein. Data stored and/or used by the computing apparatus 140 may include, for example, image data from the imaging apparatus 120, electrical signal data from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein, or any other data that may be necessary for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in at least one embodiment, the exemplary systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, mini computer, tablet computer, etc.). The exact configuration of the computing apparatus 130 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

Figure 5A:
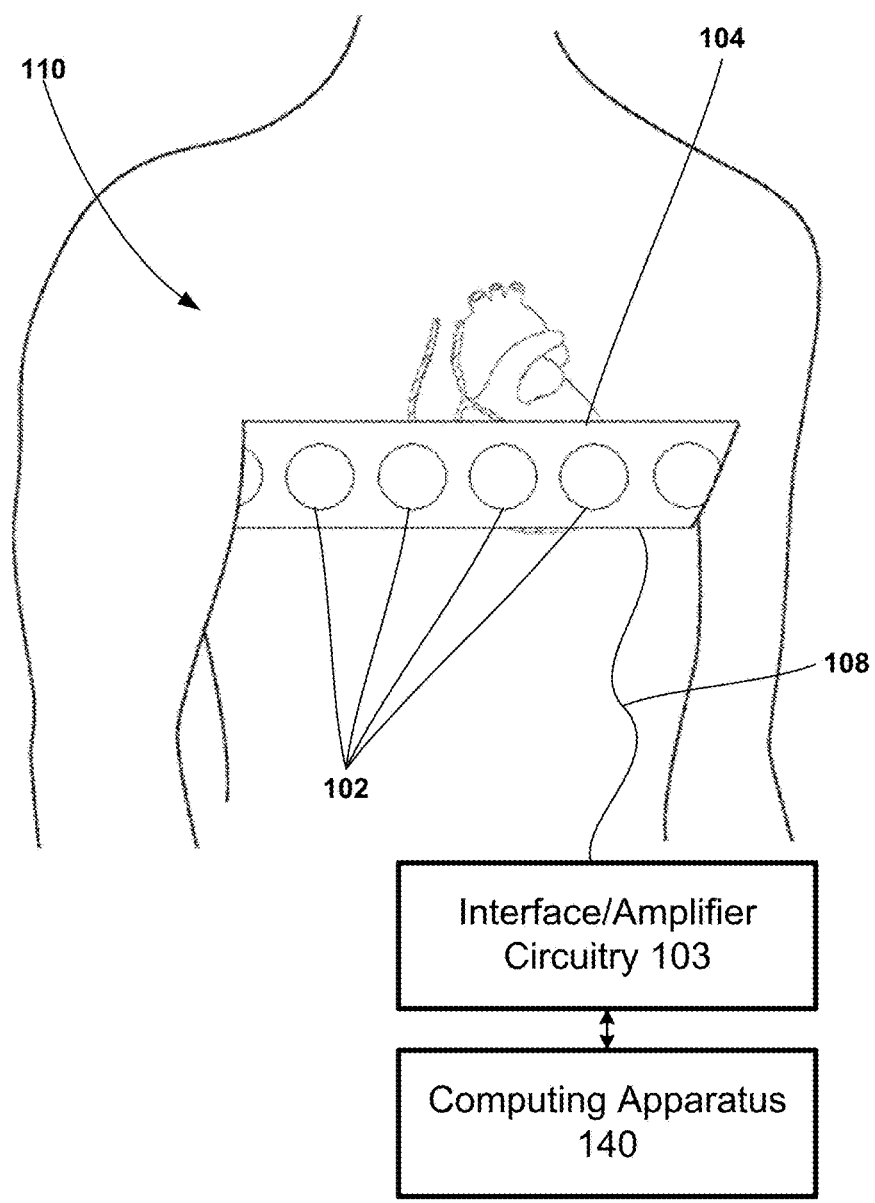
FIGS. 5A-5B are conceptual diagrams illustrating exemplary systems for measuring torso-surface potentials.
Figure 5B:
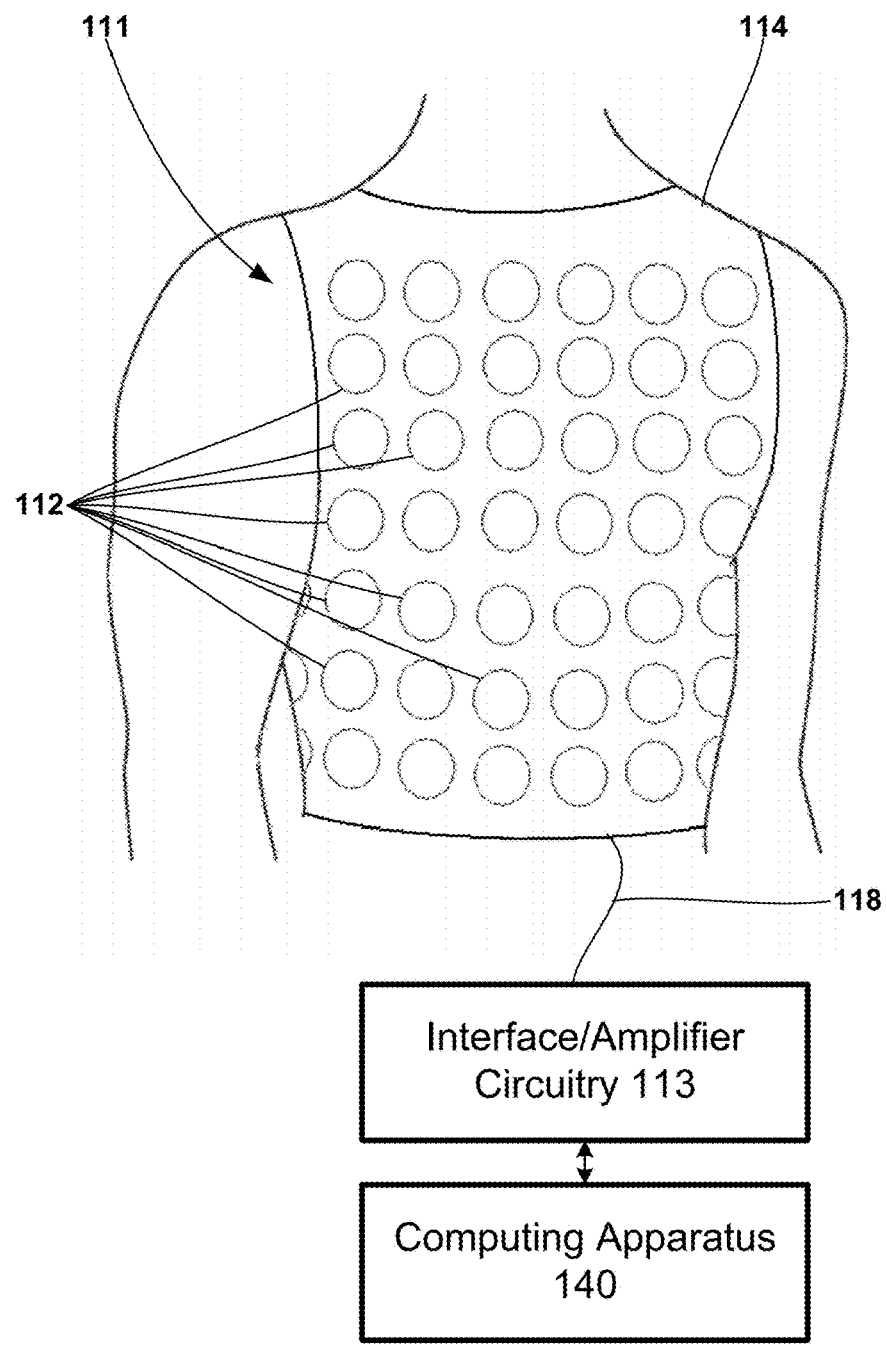

FIGS. 5A-5B are conceptual diagrams illustrating exemplary electrode systems for measuring body-surface potentials and, more particularly, torso-surface potentials. The exemplary electrode systems in FIGS. 5A-5B may be configured to measure cardiac improvement information during pacing using one or more pacing electrodes. As shown in FIG. 5A, the exemplary system 110 includes a set, or array, of electrodes 102, a strap 104, interface/amplifier circuitry 103, and computing apparatus 106. The electrodes 102 are attached, or coupled, to the strap 104 and the strap 104 is configured to be wrapped around the torso of patient such that the electrodes 102 surround the patient's heart. As further illustrated, the electrodes 102 may be positioned around the circumference of patient, including the posterior, lateral, and anterior surfaces of the torso of patient. In other examples, electrodes 102 may be positioned on any one or more of the posterior, lateral, and anterior surfaces of the torso. Further, the electrodes 102 may be electrically connected to interface/amplifier circuitry 103 via wired connection 108. The interface/amplifier circuitry 103 may be configured to amplify the signals from the electrodes 102 and provide the signals to the computing apparatus 140 such as described herein with reference to FIG. 4. Other exemplary systems may use a wireless connection to transmit the signals sensed by electrodes 102 to the interface/amplifier circuitry 103 and, in turn, the computing apparatus 140, e.g., as channels of data.

Although in the example of FIG. 5A the electrode system 110 includes a strap 104, in other examples any of a variety of mechanisms, e.g., tape or adhesives, may be employed to aid in the spacing and placement of electrodes 102. In some examples, the strap 104 may include an elastic band, strip of tape, or cloth. In other examples, the electrodes 102 may be placed individually on the torso of a patient. Further, in other examples, electrodes 102 (e.g., arranged in an array) may be part of, or located within, patches, vests, and/or other means of securing the electrodes 102 to the torso of the patient.

The electrodes 102 may be configured to surround the heart of the patient and record, or monitor, the electrical signals associated with the depolarization and repolarization of the heart after the signals have propagated through the torso of patient. Each of the electrodes 102 may be used in a unipolar configuration to sense the torso-surface potentials that reflect the cardiac signals. The interface/amplifier circuitry 103 may also be coupled to a return or indifferent electrode (not shown) which may be used in combination with each of electrodes 102 for unipolar sensing. In some examples, there may be about 12 to about 50 electrodes 102 spatially distributed around the torso of patient. Other configurations may have more or fewer electrodes 102.

The computing apparatus 140 may record and analyze the torso-surface potential signals sensed by electrodes 102 and amplified/conditioned by the interface/amplifier circuitry 103. The computing apparatus 140 may be configured to analyze the signals from the electrodes 102 to generate cardiac improvement information (e.g., provide dyssynchrony information, dyssynchrony index, etc.) usable to determine whether pacing electrodes improve cardiac functionality. Additionally, the computing apparatus 140 may be configured to provide an output to a user indicating electrical dyssynchrony in the heart of a patient. Exemplary systems and/or methods may use the cardiac functionality improvement information (e.g., dyssynchrony information) to determine whether one or more electrodes are effective for use in pacing therapy.

In some examples, the analysis of improvement in cardiac functionality by the computing apparatus 140 may take into consideration the location of electrodes lead electrodes implanted proximate cardiac tissue (e.g., electrodes located on leads implanted in the patient's heart) and/or additional tracking points based on anatomic fiducial elements or intracardiac catheters placed proximate cardiac tissue. In such examples, the computing apparatus 140 may be communicatively coupled to an imaging device 120 as shown in FIG. 4, which may provide an image that allows the computing apparatus 140 to determine coordinate locations of each of the electrodes and/or other anatomic fiducial elements or intracardiac catheters. The imaging device 120 may be configured to monitor movement of the one or more visible electrodes to provide cardiac improvement information (e.g., dyssynchrony information).

FIG. 5B illustrates another exemplary electrode system 111 that includes a plurality of electrodes 112 configured to surround the heart of the patient and record, or monitor, the electrical signals associated with the depolarization and repolarization of the heart after the signals have propagated through the torso of patient. The electrode system 110 may include a vest 114 upon which the plurality of electrodes 112 is attached, or to which they are coupled. In at least one embodiment, the plurality, or array, of electrodes 112 may be used to provide cardiac improvement information (e.g., dyssynchrony information). Similar to the electrode system 110, the electrode system 111 may include interface/amplifier circuitry 113 electrically coupled to each of the electrodes 112 through a wired connection 118 and configured to transmit signals from the electrodes 122 to a computing apparatus 140. As illustrated, the electrodes 112 may be distributed over the torso of patient, including, for example, the anterior, lateral, and posterior surfaces of the torso of patient.

The vest 114 may be formed of fabric, or any other material, with the electrodes 112 attached thereon. The vest 114 may be configured to maintain the position and spacing of electrodes 112 on the torso of the patient. Further, the vest 114 may be marked to assist in determining the location of the electrodes 112 on the surface of the torso of the patient. In some examples, there may be about 25 to about 256 electrodes 112 distributed around the torso of the patient, though other configurations may have more or fewer electrodes 112.

The exemplary systems, apparatus, methods, and/or interfaces described herein are configured to identify one or more optimal electrical vectors for delivering cardiac therapy, and the systems including electrodes and computing apparatus described herein with reference to FIGS. 1-5 may utilize the exemplary systems, apparatus, methods, and/or interfaces. More specifically, the exemplary systems, apparatus, methods, and/or interfaces may be used to determine which electrical vectors defined by one or more electrodes in the systems of FIGS. 1-5 may be optimal for delivering pacing therapy to tissue of the patient and/or to assist a user in navigating, or locating, one or more electrodes to deliver pacing to the tissue of the patient about the optimal electrical vectors.

For example, when the leads 18, 20, 22 of the system 10 of FIGS. 1-3 are located, or implanted, in a patient's heart, a plurality of different electrical vectors for delivering cardiac therapy be defined by the electrodes 40, 42, 44, 45, 46, 47, 48, 50, 58, 62, 64, 66. As such, the exemplary systems, apparatus, methods, and/or interfaces may be used with the system 10 of FIGS. 1-3 to determine which electrodes 40, 42, 44, 45, 46, 47, 48, 50, 58, 62, 64, 66 and which electrical vectors defined by the electrodes 40, 42, 44, 45, 46, 47, 48, 50, 58, 62, 64, 66 may be optimal for delivering effective electrical therapy to the cardiac tissue of the patient.

Figure 6:
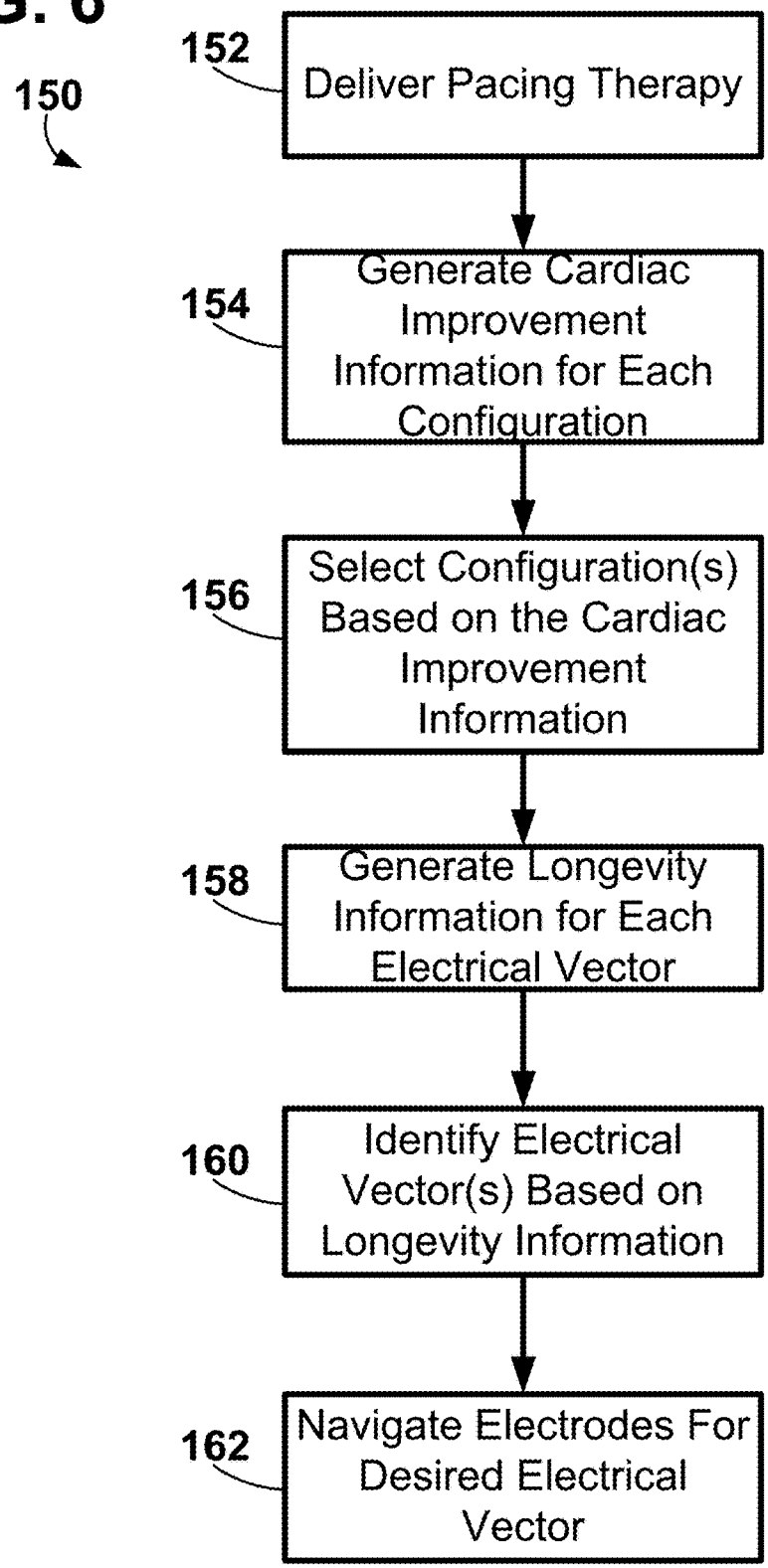
FIG. 6 is a block diagram of an exemplary method of identifying an optimal electrical vector.

An exemplary method 150 for identifying one or more optimal electrical vectors is depicted in FIG. 6. The method 150 includes delivering pacing therapy 152 using a plurality of electrodes in a plurality of different pacing configurations. The pacing therapy 152 may utilize one or more electrodes such as the electrodes 40, 42, 44, 45, 46, 47, 48, 50, 58, 62, 64, 66 of the system 10. For example, each electrode (e.g., as a cathode) may be used individually to deliver pacing therapy (e.g., using the same or a different anode). In other words, one electrode at a time may be used to deliver pacing therapy. Further, for example, more than one electrode (e.g., two electrodes, three electrodes, etc.) may be used simultaneously to deliver pacing therapy. In at least one embodiment, more than one electrode (e.g., two electrodes, three electrodes, etc.) may be used simultaneously to deliver pacing therapy (e.g., if none of the electrodes used individually achieves capture, if none of the electrodes used individually provides cardiac improvement (e.g., significant cardiac improvement, sufficient cardiac improvement, etc.), etc.). In other words, more than one electrode at a time may be used to deliver pacing therapy. Additionally, one or more pacing electrodes may deliver more than one pacing pulse (e.g., each pacing pulse having a selected pacing width, each pacing pulse separated by a selected separation time period, etc.) if, e.g., none of the electrodes used individually achieves capture, if none of the electrodes used individually provides cardiac improvement (e.g., significant cardiac improvement, sufficient cardiac improvement, etc.).

In essence, the exemplary method 150 may deliver pacing therapy using a plurality of different pacing configurations using the plurality of electrodes. In some embodiments, a common anode may be used for each different pacing configuration. In other embodiments, each different pacing configuration may use a different anode.

For each different pacing configuration, the method 150 may generate cardiac improvement information 154. The cardiac improvement information may be defined as information that is representative of a change in mechanical and/or electrical cardiac functionality resulting from pacing. In other words, the cardiac improvement information may be indicative of improvement of cardiac functionality from baseline cardiac functionality. The baseline cardiac functionality may be cardiac functionality without any pacing therapy being delivered to the patient.

In one or more embodiments, the cardiac improvement information may include dyssynchrony information. The dyssynchrony information may also be referred to as measures of electrical heterogeneity. Dyssynchrony information may be defined as information indicative of the mechanical and/or electrical dyssynchrony of the heart. In at least one embodiment, the dyssynchrony information may include a standard deviation of ventricular activation times corresponding to electrodes on the surface array. Further, regional dyssynchrony may be also computed from the standard deviation of activation times corresponding to electrodes located in certain anatomic areas of the torso, for e.g. electrodes on the left side of the torso would be used to compute regional LV dyssynchrony. The dyssynchrony information may be generated using one or more various systems and/or methods. Dyssynchrony information may be generated using an array, or a plurality, of surface electrodes and/or imaging systems as described in U.S. Pat. App. Pub. No. 2012/0283587 A1 published Nov. 8, 2012 and entitled "ASSESSING INRA-CARDIAC ACTIVATION PATTERNS AND ELECTRICAL DYSSYNCHRONY," U.S. Pat. App. Pub. No. 2012/0284003 A1 published Nov. 8, 2012 and entitled "ASSESSING INTRA-CARDIAC ACTIVATION PATTERNS", and U.S. Pat. No. 8,180,428 B2 issued May 15, 2012 and entitled "METHODS AND SYSTEMS FOR USE IN SELECTING CARDIAC PACING SITES," each of which is incorporated herein by reference in its entirety.

Dyssynchrony information may include one or more dyssynchrony indices. For example, one of the indices of electrical dyssynchrony may be a standard deviation index computed as the standard deviation of the activations-times (SDAT) of some or all of the electrodes on the surface of the torso of patient. In some examples, the SDAT may be calculated using the estimated cardiac activation times over the surface of a model heart.

A second example index of dyssynchrony may be a range of activation times (RAT) which may be computed as the difference between the maximum and the minimum torso-surface or cardiac activation times, e.g., overall, or for a region. The RAT reflects the span of activation times while the SDAT gives an estimate of the dispersion of the activation times from a mean. The SDAT also provides an estimate of the heterogeneity of the activation times, because if activation times are spatially heterogeneous, the individual activation times will be further away from the mean activation time, indicating that one or more regions of heart have been delayed in activation. In some examples, the RAT may be calculated using the estimated cardiac activation times over the surface of a model heart.

A third example index of electrical dyssynchrony estimates the percentage of surface electrodes located within a particular region of interest for the torso or heart, whose associated activation times are greater than a certain percentile, for example the 70th percentile, of measured QRS complex duration or the determined activation times for surface electrodes. The region of interest may be a posterior, left anterior, and/or left-ventricular region, as examples. This index, the percentage of late activation (PLAT), provides an estimate of percentage of the region of interest, e.g., posterior and left-anterior area associated with the left ventricular area of heart, which activates late. A large value for PLAT may imply delayed activation of a substantial portion of the region, e.g., the left ventricle, and the potential benefit of electrical resynchronization through CRT by pre-exciting the late region, e.g., of left ventricle. In other examples, the PLAT may be determined for other subsets of electrodes in other regions, such as a right anterior region to evaluate delayed activation in the right ventricle. Furthermore, in some examples, the PLAT may be calculated using the estimated cardiac activation times over the surface of a model heart for either the whole heart or for a particular region, e.g., left or right ventricle, of the heart.

In one or more embodiments, the cardiac improvement information may include indicators of favorable changes in global cardiac electrical activation such as, e.g., described in Sweeney et al., "Analysis of Ventricular Activation Using Surface Electrocardiography to Predict Left Ventricular Reverse Volumetric Remodeling During Cardiac Resynchronization Therapy," Circulation, 2010 Feb. 9, 121(5): 626-34 and/or Van Deursen, et al., "Vectorcardiography as a Tool for Easy Optimization of Cardiac Resynchronization Therapy in Canine LBBB Hearts," Circulation Arrhythmia and Electrophysiology, 2012 Jun. 1, 5(3): 544-52, each of which is incorporated herein by reference in its entirety. Cardiac improvement information may also include measurements of improved cardiac mechanical function measured by imaging or other systems to track motion f implanted leads within the heart as, e.g., described in Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, 2010 February, 21(2): 219-22, Sperzel et al., "Intraoperative Characterization of Interventricular Mechanical Dyssynchrony Using Electroanatomic Mapping System—A Feasibility Study," Journal of Interventional Cardiac Electrophysiology, 2012 November, 35(2): 189-96, and/or U.S. Pat. App. Pub. No. 2009/0099619 A1 entitled "METHOD FOR OPTIMIZAING CRT THERAPY" and published on Apr. 16, 2009, each of which is incorporated herein by reference in its entirety.

In one or more embodiments, the cardiac improvement information may be generated by tracking lead motion and inter-electrode distances with fluoroscopy to generate at least one metric (e.g., value(s), functions, comparisons, differences, averages, slopes, etc.) that correlates with cardiac contractility. For example, a contractility curve may be generated based on the variation in distance between the RV and LV electrode-tips during the course of one or more cardiac cycles and one or more metrics relating to fractional shortening may be derived from this curve. In another embodiment, multiple points on intracardiac leads and/or catheter systems may be tracked during course of one or more cardiac cycles to generate metrics relating to contractility or global cardiac mechanical dyssynchrony.

In at least one embodiment, a computing apparatus such as the computing apparatus 140 described herein with reference to FIG. 4 may be used to measure a dyssynchrony index during intrinsic rhythm and during pacing with each pacing configuration or electrode to generate cardiac functionality information used to select one or more pacing configurations or electrodes to be possibly used in one or more optimal pacing vectors. For example, a physician may place a LV lead in a target location and a user may initiate CRT pacing from the programmer/analyzer. For each of a plurality of CRT pacing configurations, the system may be configured to detect the pacing parameters displayed on the programmer/analyzer screen (e.g., using character recognition from VGA output), and then, the system may measure a dyssynchrony index. The CRT pacing configurations may be automatically, or manually, changed on a programmer/analyzer. Then, the system may classify each of the electrodes, or electrode configurations, as one of "improved," "neutral," or "worsened" using the dyssynchrony measurements.

In at least one embodiment, changes in dyssynchrony during CRT pacing may be measured from each LV electrode as the cathode at a common A-V delay (e.g., less than 60 milliseconds from the intrinsic AV time) ensuring sufficient energy for cathode capture and/or to avoid fusion of the pacing depolarization with the intrinsic depolarization. Further, a common anode may be selected for these preliminary evaluations such as, e.g., a RV coil. Cathode capture can be verified by morphology of a LV cathode to RV coil electrocardiogram.

In at least one embodiment, if poor dyssynchrony is measured, the exemplary method may switch to higher amplitudes to encourage some anodal capture and/or switch to multi-site pacing (e.g., pacing using more than one electrode) to, e.g., see if dyssynchrony improves.

Based on the cardiac improvement information, the method 150 may select one or more electrodes 156. To select the one or more pacing configurations, the cardiac improvement information may provide one or more numerical metrics or values (e.g., value(s), functions, differences, comparisons, averages, slopes, etc.) that may be compared against each other and/or one or more threshold values. The pacing configurations having the best cardiac improvement information and/or metrics or values exceeding selected thresholds may be selected to be used in, or defining, one or more (e.g., one, two or more, a plurality, etc.) different pacing vectors.

For example, dyssynchrony information may include a dyssynchrony improvement value for each pacing configuration. The dyssynchrony improvement value may be generated by monitoring the dyssynchrony of the patient's heart without resynchronization pacing therapy to establish a baseline, monitoring the dyssynchrony of the patient's heart during pacing using each electrode (or electrode configuration), and comparing the baseline dyssynchrony to the dyssynchrony during resynchronization pacing to provide a dyssynchrony improvement value for each electrode (or electrode configuration). In at least one embodiment, the dyssynchrony improvement value for each pacing configuration may be compared to a threshold value and each pacing configuration exceeding the threshold value may be selected.

The dyssynchrony improvement values themselves may assist in defining, or selecting the threshold value. Generally, the threshold may be defined as a decreasing function of the maximal dyssynchrony improvement value (e.g., maximal relative improvement in resynchronization). More specifically, the threshold value may be calculated by multiplying a factor by the maximal, or maximum, dyssynchrony improvement value.

Further, the factor used to calculate the threshold value may be selected based on the maximum generated dyssynchrony improvement value. In at least one embodiment, if a maximal dyssynchrony improvement value, or maximal relative improvement in resynchronization value, is between 0% and 5%, then the factor may be set of 0.9. If the maximal dyssynchrony improvement value is between 5% and 10%, then the factor may be set to 0.8. If the maximal dyssynchrony improvement value is between 10% and 25%, then the factor may be set to 0.75. If the maximal dyssynchrony improvement value is above 25%, then the factor may be set to 0.7. A threshold for a maximal dyssynchrony improvement value means that all pacing configurations and/or electrodes with a resynchronization efficacy greater than the threshold multiplied by the maximal dyssynchrony improvement value should be selected (e.g., selected to be possibly used in one or more optimal pacing vectors).

The one or more pacing configurations and/or electrodes selected based on the cardiac improvement information 156 may define, or be used to form, one or more electrical vectors configured to deliver therapy to the patient's heart. For example, if a first left ventricular electrode and a second left ventricular electrode are selected based on the cardiac improvement information, one or more electrical vectors may be defined between the first left ventricular electrode and one or all of the remaining electrodes and one or more electrical vectors may be defined between the second left ventricular electrode and one or all of the remaining electrodes.

In other words, the selection of one or more pacing configurations and/or electrodes based on the cardiac improvement information 156 may provide one or more electrical vectors that may be used to deliver therapy. To determine whether the one or more electrical vectors are optimal, the method 150 may take into consideration information such as longevity information for each electrical vector 158, whether the electrical vector is stimulates the phrenic nerve, etc.

For example, generated longevity information 158 may include an energy expenditure value for each electrical vector, which can be determined based on a capture threshold for each electrical vector, an impedance value for each electrical vector, a pulse width for each electrical vector (e.g., required for capture), information regarding each pacing pulse for multi-site pacing configurations, etc. Energy expenditure may be expressed in actual or relative estimated energy usage or actual or relative predicted battery longevity when an IMD operates using a particular parameter selection.

One or more processes and/or methods disclosed in U.S. Pat. App. Pub. No. 2012/0101543 A1 filed on Oct. 21, 2010 and entitled "CAPTURE THRESHOLD MEASUREMENT FOR SELECTION OF PACING VECTOR," U.S. Pat. App. Pub. No. 2012/0101546 A1 filed on Jul. 29, 2011 and entitled "METHOD AND APPARATUS TO DETERMINE THE RELATIVE ENERGY EXPENDITURE FOR A PLURALITY OF PACING VECTORS," U.S. Pat. App. Pub. No. 2013/0030491 A1 filed on Jul. 28, 2011 and entitled "METHOD FOR DISCRIMINATING ANODAL AND CATHODAL CAPTURE," and U.S. patent application Ser. No. 13/790,683 filed on Mar. 8, 2013 and entitled "CAPTURE THRESHOLD MEASUREMENT FOR SELECTION OF PACING VECTOR," each of which is incorporated herein by reference in its entireties, may be implemented to provide cardiac improvement information such as longevity information, capture thresholds, impedance, etc. for one or more selected electrical vectors.

Figure 11:
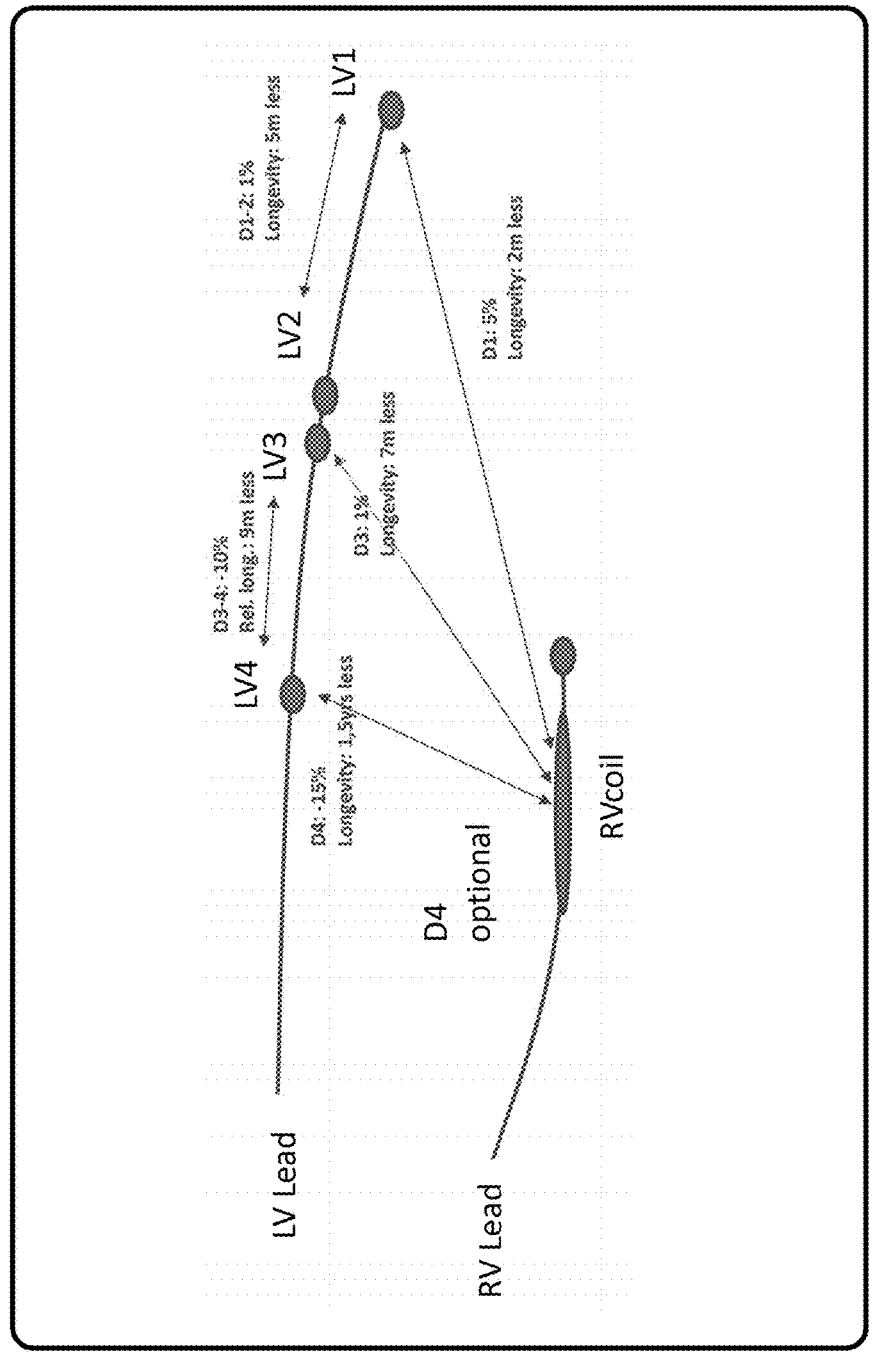
FIG. 11 is an exemplary graphical user interface depicting a graphical representation of a pair of leads and cardiac improvement information and longevity information depicted proximate the electrodes of the leads.

After longevity information has been generated for each electrical vector 158, the method 150 may identify one or more optimal electrical vectors based on the longevity information 160. For example, the method 150 may identify the optimal electrical vectors and automatically configure the pacing system to use the optimal electrical vectors for pacing. Further, for example, the method 150 may generate a graphical user interface 132 depicting each of the selected electrical vectors and their associated longevity information, e.g., as shown in FIG. 11. Further, the method 150 may identify the selected electrical vectors having optimal longevity information on the graphical user interface 132, e.g., by highlighting, circles, arrows, etc. (e.g., as shown in FIG. 9).

In one or more embodiments, the method 150 may identify the most optimal electrical vector, e.g., by identifying the electrical vector having one or more of the greatest longevity, lowest capture threshold, smallest impedance, etc.

Additionally, whether the one or more selected electrical vectors stimulate the phrenic nerve may be used to identify the one or more optimal electrical vectors. For example, the method 150 may include determining whether each electrical vector stimulates the phrenic nerve and identifying the optimal electrical vector of the plurality of electrical vectors based on an absence of phrenic nerve stimulation.

One or more processes and/or methods disclosed in U.S. Pat. App. Pub. No. 2012/0296388 A1 filed on May 17, 20120 and entitled "PHRENIC NERVE STIMULATION DETECTION USING HEART SOUNDS," U.S. Pat. App. Pub. No. 2012/0296387 A1 filed on Nov. 22, 2012 and entitled "PHRENIC NERVE STIMULATION DETETION USING HEART SOUNDS," U.S. Pat. No. 8,295,943 B2 issued on Oct. 23, 2012 and entitled "IMPLANTABLE MEDICAL LEAD WITH BIASED ELECTRODE," and U.S. Pat. App. Pub. No. 2009/0054941 A1 filed on Aug. 20, 2008 and entitled "STIMULATION FIELD MANAGEMENT," each of which is incorporated herein by reference in their entirety, may be implemented to provide phrenic nerve stimulation information (e.g., for use in determining whether one or more electrical vectors stimulate the phrenic nerve).

After the method 150 has identified one or more optimal electrical vectors based on the longevity information 160, the method 150 may further 162 allow a user (e.g., physician) to navigate, or locate, one or more electrodes 162 (e.g., implantable electrodes on one or more leads, wireless/leadless electrodes, etc.) to one or more regions proximate a patient's heart to provide pacing therapy, e.g., using the one or more identified optimal electrical vectors 160. For example, a graphical user interface 132, such as shown in FIG. 11 described further herein, may include a graphical depiction and/or actual imaging (e.g., using imaging apparatus 120 of FIG. 4) of a patient's heart in conjunction with the identified one or more optimal pacing vectors. Using the graphical user interface 132, a user may navigate, or locate, the one or more electrodes in the desired locations based on the identified optimal electrical vectors 160.

Exemplary systems, methods, apparatus, and interfaces for electrode location selection and implantation may be described in U.S. patent application Ser. No. 13/916,353 filed on Jun. 12, 2013 and entitled "Implantable Electrode Location Selection," U.S. patent application Ser. No. 13/916,377 filed on Jun. 12, 2013 and entitled "Implantable Electrode Location Selection," U.S. Provisional Patent Application No. 61/817,483 filed on Apr. 30, 2013 and entitled "Identifying Effective Electrodes," U.S. Provisional Patent Application 61/913,795 entitled "Systems, Methods, and Interfaces for Identifying Effective Electrodes" and filed on Dec. 9, 2013, and U.S. patent application entitled "Systems, Methods, and Interfaces for Identifying Effective Electrodes" and filed on even date herewith, each of which is incorporated herein by reference in its entireties.

Figure 7:
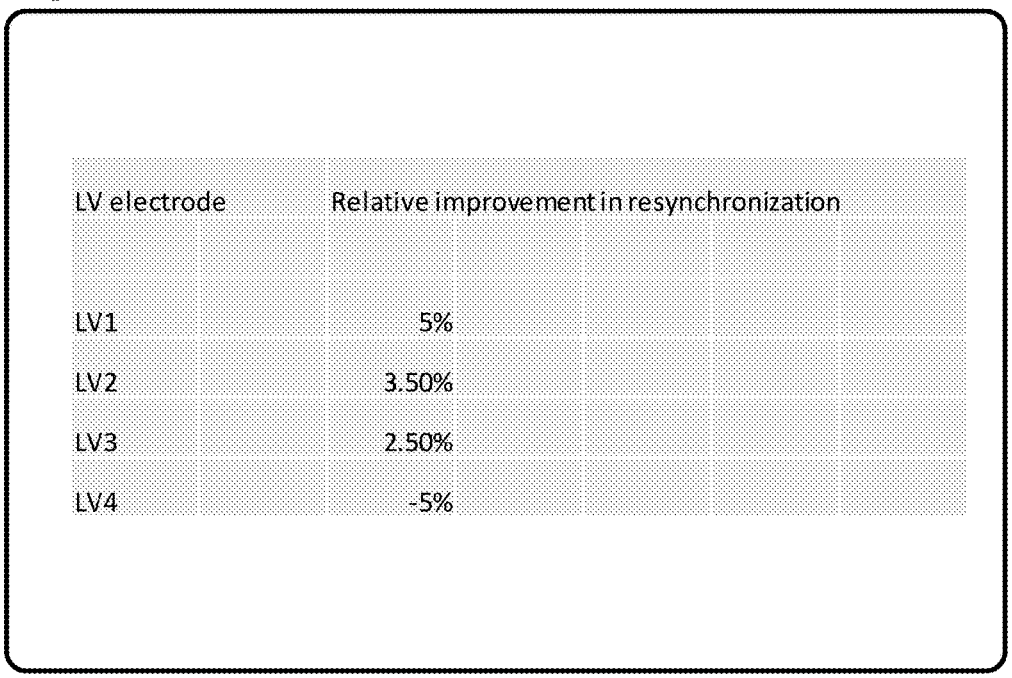
FIG. 7 is an exemplary graphical user interface depicting a table of cardiac improvement information for a plurality of electrodes.

Exemplary graphical user interfaces 132 including displays and tables used and/or generated by the exemplary methods and/or systems described herein for identifying one or more optimal electrical vectors are shown in FIGS. 7-11. As shown in FIG. 7, cardiac improvement information has been generated for four different left ventricular electrodes (LV1, LV2, LV3, LV4). Since the maximal improvement is 5% in this example, the factor for generating the threshold value may be set to 0.9 so all electrodes with relative improvement greater than or equal to 0.9 multiplied by 5% (i.e., the maximal improvement) may be considered equivalent/effective, and thus, may be considered as the cathode for optimal vector selection. In this example, only LV1 has a relative improvement greater than or equal to 4.5. For lower relative improvements (e.g., 0% to 5%) as depicted in FIG. 6, the factor for generating the threshold for equivalence should be high (e.g., 0.9).

Figure 8:
FIG. 8 is another exemplary graphical user interface depicting a table of cardiac improvement information for a plurality of electrodes.

As shown in the exemplary graphical user interface 132 of FIG. 8, cardiac improvement information has been again generated for four different left ventricular electrodes (LV1, LV2, LV3, LV4). Since maximal improvement is 40%, the factor for generating the threshold may be set to 0.7 so all electrodes with relative improvement greater than or equal to 0.7 multiplied by 40% (i.e., the maximal improvement) may be considered equivalent/effective, and thus, may be considered as the cathode for optimal vector selection. In this exemplary, two electrodes, LV2 and LV3, have a relative improvement greater than or equal to 28%. For larger improvements (e.g., greater than 28%) as depicted in FIG. 7, the factor for generating the threshold for equivalence can be more relaxed (e.g., 0.7).

Longevity information may be generated for all possible vectors with the selected electrodes, LV2 and LV3, of FIG. 7 as cathodes, and may be presented in the exemplary graphical interface 132 depicting a table as shown in FIG. 9. As shown, vectors LV2-LV3 and LV2-LV4 are indicated as having maximum relative longevity. Additionally, phrenic nerve stimulation information is depicted in the table of FIG. 9.

Vector LV2-LV3 may be determined as being the most optimal vector based on the longevity information and the phrenic nerve stimulation information (e.g., such as stimulation being absent). As shown in FIG. 9, an indication 172 (i.e., an oval) may be depicted on a graphical user interface used to select electrical vectors to indicate the most optimal electrical vector.

Although not shown, all vectors corresponding to the chosen LV cathodes and which do not have associated phrenic nerve stimulation may be sorted in descending order of longevity (e.g., max longevity at the top) to make the selection convenient. In this example, the system may automatically select or the implanter or physician may select LV2-LV3 as the pacing vector to be used for pacing therapy.

An exemplary graphical user interface 132 depicting a table of longevity information, phrenic nerve stimulation, and cardiac improvement information for a plurality of electrical vectors is shown in FIG. 10. In this example, the cardiac improvement information is displayed simultaneously with the longevity information and phrenic nerve stimulation information. As shown, the LV3-LV4 vector may be identified as being the most optimal electrical vector because, e.g., electrode LV3 provided a change in dyssynchrony index of −10% (e.g., an improvement of 10%) and the relative longevity has been determined to be 9 months less than a maximum longevity. Although the dyssynchrony index is indicated as a negative value (i.e., −10%) when indicating an improvement and a positive value when indicating a worsened condition, it to be understood that the dyssynchrony index may be indicated as positive value when indicating an improvement and a negative value when indicating a worsened condition.

An exemplary graphical user interface 132 including a graphical representation of a pair of leads, a LV lead and a RV lead, is depicted in FIG. 11, which define the electrode vectors shown and described with respect to FIG. 10. Although not shown, the graphical user interface of FIG. 11 may further include the table of FIG. 10, e.g., to display information to a physician, to allow a physician to select one or more optimal vectors, to identify the one or more optimal vectors graphically, etc. As shown, cardiac improvement information and longevity information are depicted proximate the electrical vectors defined by the electrodes of the leads.

Generally, any factor (e.g., cardiac improvement information, longevity information, phrenic nerve stimulation information, etc.) alone or in combination may be used to identify one or more optimal electrical vectors. For example, dyssynchrony information may be used in combination with phrenic nerve stimulation information, dyssynchrony information may be used in combination with longevity information, longevity information may be used alone, dyssynchrony information may be used alone, etc.

The graphical user interfaces 132 described herein with reference to FIGS. 7-11 may be provided to users such as physicians to assist them in determining which of the optimal electrical vectors to use for pacing therapy and/or navigating one or more electrodes (e.g., implantable electrodes on one or more leads) to one or more regions of a patient's heart to perform pacing at the optimal electrical vectors.

Figure 12:
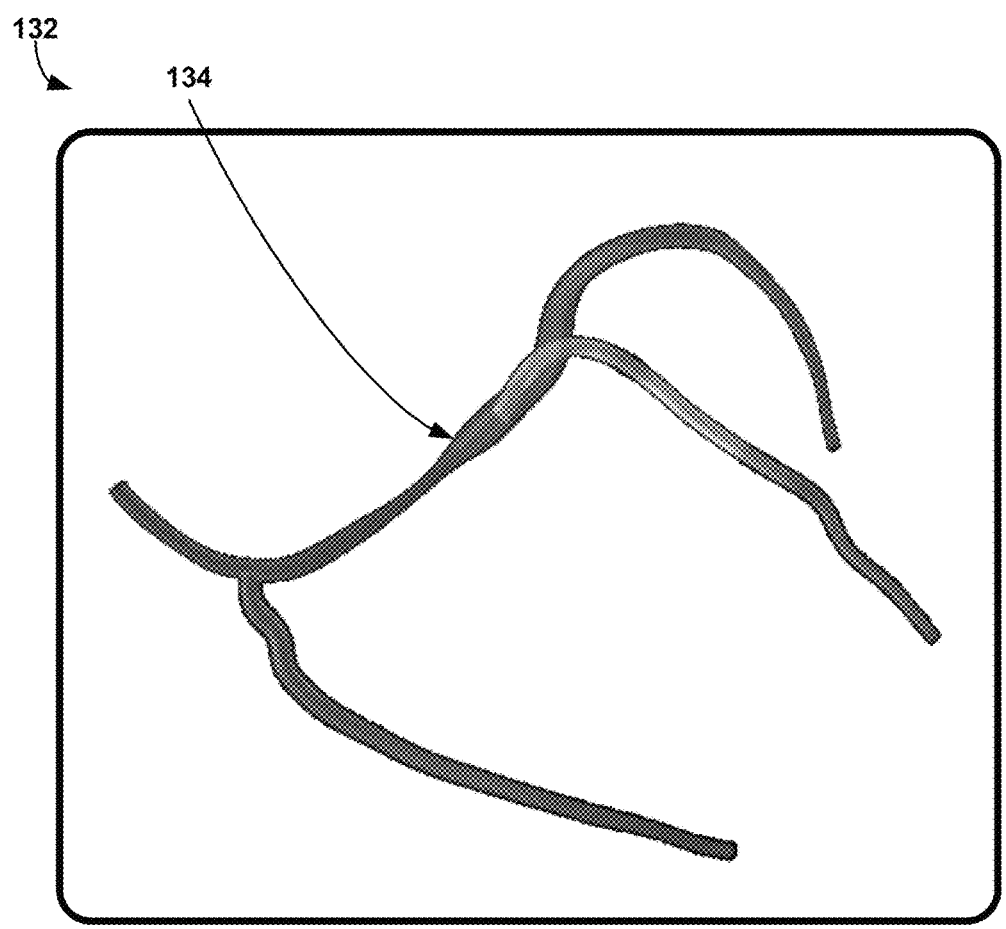
FIG. 12 is an exemplary graphical user interface depicting blood vessel anatomy configured to assist a user in navigating an implantable electrode to a region of a patient's heart for cardiac therapy.

An exemplary graphical user interface 132 including blood vessel anatomy 134 of a patient's heart is shown in FIG. 12 that may be used by a user to navigate an implantable electrode to a region of the patient's heart. The blood vessel anatomy as well as other data such as mechanical motion information, etc. of the heart may be captured using the imaging apparatus 120 described herein, which may be configured to image at least a portion of blood vessel anatomy of the patient's heart and provide image data used by the computing apparatus 140 to provide mechanical motion information or data. The data or information depicted on the blood vessel anatomy of the patient's heart in FIG. 12 may be further monitored, or gathered, using the electrode apparatus 110 described herein.

A user may view and/or use the graphical user interface 132 of FIG. 12 to determine, or identify, one or more candidate site regions of the displayed portion region of the patient's heart for implantation of implantable electrodes. For example, a user may view mechanical motion information, e.g., grey-scaling or color-coding applied to the blood vessel anatomy in FIG. 12, and identify a candidate site region of the patient's heart based on the mechanical motion information. For example, a user may identify one or more regions having, e.g., mechanical motion times greater than a threshold, having the longest mechanical motion time, etc.

Figure 13:
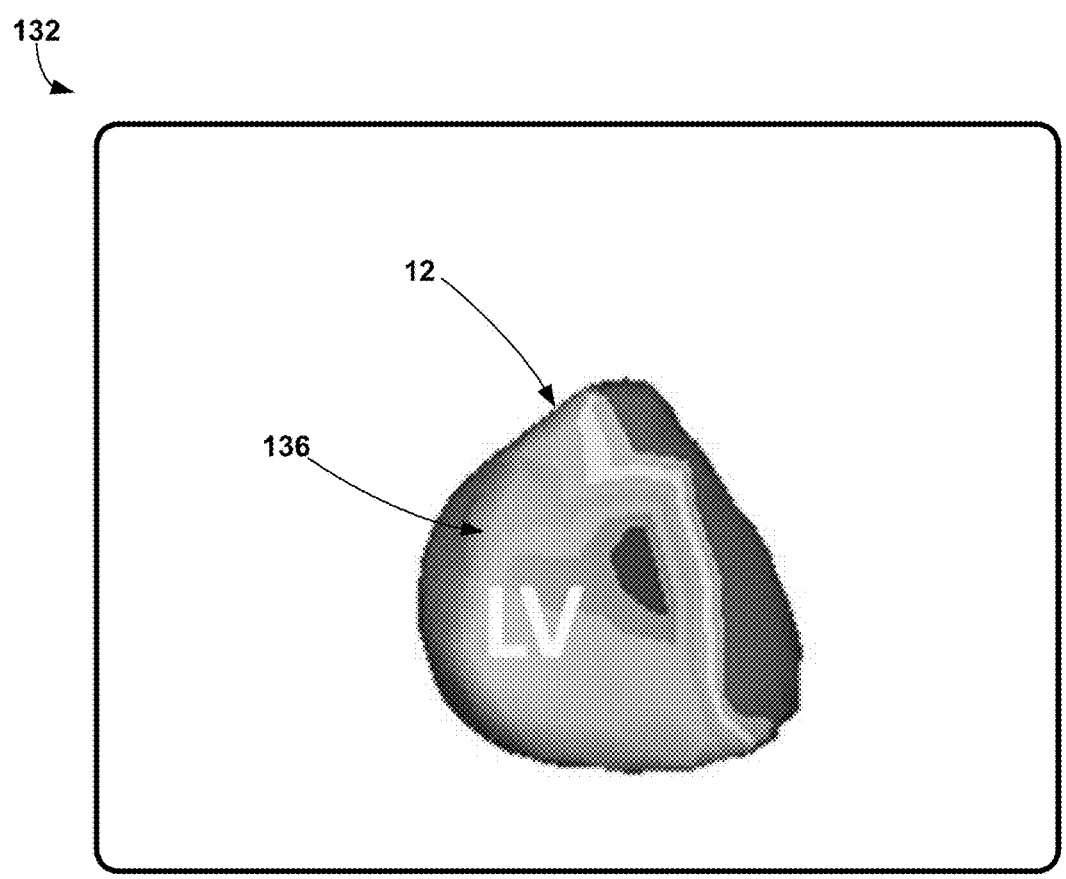
FIG. 13 is an exemplary graphical user interface depicting a human heart including activation times mapped thereon configured to assist a user in navigating an implantable electrode to a region of a patient's heart for cardiac therapy.

Another exemplary graphical user interface 132 including a graphical depiction of a patient's heart 12 is shown in FIG. 13 that may be used by a user to navigate an implantable electrode to a region of the patient's heart. More specifically, a posterior side of a human heart 12 is depicted in the graphical user interface 132 of FIG. 13 with surrogate electrical activation times 136 color-coded, or gray-scaled, across the surface of the heart 12. As used herein, surrogate electrical activation data (e.g., surrogate electrical activation times, surrogate electrical activation time maps, etc.) may be defined as data representative of actual, or local, electrical activation data of one or more regions of the patient's heart. For example, electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart.

As shown, the posterolateral left ventricle region shows late activation (e.g., about 150 milliseconds). In other embodiments, both a posterior and anterior side of a human heart may be graphically depicted and overlaid with electrical activation information. The data or information depicted on the patient's heart 12 in FIG. 13 may be further monitored, or gathered, using the electrode apparatus 110 described herein.

The techniques described in this disclosure, including those attributed to the IMD 16, the programmer 24, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A system for use in cardiac therapy comprising:
electrode apparatus comprising a plurality of electrodes configured to be located proximate tissue of a patient for pacing;
display apparatus comprising a graphical user interface, wherein the graphical user interface is configured to present information for use in assisting a user in at least one of assessing a patient's cardiac health, evaluating and adjusting cardiac therapy delivered to a patient, and navigating at least one implantable electrode to a region of the patient's heart; and
computing apparatus coupled to the electrode apparatus and display apparatus and configured to:
deliver pacing therapy to the patient using each pacing configuration of a plurality of different pacing configurations, wherein each pacing configuration uses one or more electrodes of the plurality of electrodes to deliver electrical pacing stimulation,
generate cardiac improvement information for each pacing configuration, wherein the cardiac improvement information is representative of a change in mechanical and/or electrical cardiac functionality resulting from pacing delivered using each pacing configuration,
select one or more pacing configurations of the plurality of different pacing configurations that each used one or more electrodes of the plurality of electrodes to deliver pacing stimulation based on the cardiac improvement information, wherein each of the one or more selected pacing configurations that used one or more electrodes of the plurality of electrodes to deliver pacing stimulation are usable with one or more other electrodes to define a plurality of electrical vectors, wherein each of the plurality of electrical vectors are defined by at least one of the one or more electrodes used by the one or more selected pacing configurations to deliver pacing stimulation and at least one of the one or more other electrodes,
generate longevity information for each electrical vector of the plurality of electrical vectors, wherein the longevity information comprises at least energy expenditure expressed in actual or predicted battery longevity,
identify one or more optimal electrical vectors of the plurality of electrical vectors based on the longevity information, and
display, on the graphical user interface, information for use in assisting a user in at least one of assessing a patient's cardiac health, evaluating and adjusting cardiac therapy delivered to a patient, and navigating at least one implantable electrode to a region of the patient's heart, wherein the information comprises the identified one or more optimal electrical vectors.

2. The system of claim 1, wherein generating cardiac improvement information for each pacing configuration comprises generating dyssynchrony information for each pacing configuration by monitoring heart function using at least one of a plurality of surface electrodes during pacing and cardiac imaging apparatus during pacing.

3. The system of claim 2, wherein the dyssynchrony information comprises a dyssynchrony improvement value for each pacing configuration, wherein the dyssynchrony improvement value is generated by comparing baseline dyssynchrony to paced dyssynchrony during pacing using each pacing configuration.

4. The system of claim 3, wherein selecting one or more pacing configurations based on the cardiac improvement information comprises:
defining a threshold value based on the dyssynchrony information; and
selecting one or more pacing configurations having a dyssynchrony improvement value greater than the threshold value.

5. The system of claim 1, wherein the electrode apparatus further comprises at least one lead, wherein the plurality of electrodes are coupled to the at least one lead.

6. The system of claim 1, wherein a common anode is used when delivering pacing therapy using each pacing configuration of the plurality of different pacing configurations to be used to generate cardiac improvement information.

7. The system of claim 1, wherein the control module is further configured to deliver pacing therapy using at least one pacing configuration that uses two or more electrodes of the plurality of electrodes per cardiac cycle if the cardiac improvement information generated for each pacing configuration that uses one electrode of the plurality of electrodes does not meet a threshold criteria.

8. The system of claim 1, wherein generating longevity information for each electrical vector of the plurality of electrical vectors comprises determining at least one of a capture threshold for each electrical vector and an impedance value for each electrical vector.

9. The system of claim 1, wherein the control module is further configured to:
determine whether each electrical vector stimulates the phrenic nerve; and
identify the one or more optimal electrical vectors of the plurality of electrical vectors based on an absence of phrenic nerve stimulation.

10. The system of claim 1, wherein identifying the one or more optimal electrical vectors of the plurality of electrical vectors based on the longevity information comprises identifying the electrical vector having at least one of the greatest longevity, lowest capture threshold, and smallest impedance.

11. The system of claim 1, wherein the computing apparatus is further configured to identify, on the graphical user interface, the identified one or more optimal electrical vectors on a graphical depiction of at least a portion of anatomy of the patient's heart.

12. The system of claim 1, wherein the computing apparatus is further configured to:
   determine one or more candidate regions proximate the patient's heart for implantation of an implantable electrode based on the identified one or more optimal electrical vectors; and
   identify, on the graphical user interface, the one or more candidate site regions on a graphical depiction of at least a portion of anatomy of the patient's heart for implantation of the implantable electrode.

13. A method for use in cardiac therapy comprising:
   delivering pacing therapy using each pacing configuration of a plurality of different pacing configurations, wherein each pacing configuration uses one or more electrodes of a plurality of electrodes to deliver electrical pacing stimulation;
   generating cardiac improvement information for each pacing configuration, wherein the cardiac improvement information is representative of a change in mechanical and/or electrical cardiac functionality resulting from pacing delivered using each pacing configuration;
   selecting one or more pacing configurations of the plurality of different pacing configurations that each used one or more electrodes of the plurality of electrodes to deliver pacing stimulation based on the cardiac improvement information, wherein each of the one or more selected pacing configurations that used one or more electrodes of the plurality of electrodes to deliver pacing stimulation are usable with one or more other electrodes to define a plurality of electrical vectors, wherein each of the plurality of electrical vectors are defined by at least one of the one or more electrodes used by the one or more selected pacing configurations to deliver pacing stimulation and at least one of the one or more other electrodes;
   generating longevity information for each electrical vector of the plurality of electrical vectors, wherein the longevity information comprises at least energy expenditure expressed in actual or predicted battery longevity;
   identifying one or more optimal electrical vectors of the plurality of electrical vectors based on the longevity information; and
   displaying, on the graphical user interface, information for use in assisting a user in at least one of assessing a patient's cardiac health, evaluating and adjusting cardiac therapy delivered to a patient, and navigating at least one implantable electrode to a region of the patient's heart, wherein the information comprises the identified one or more optimal electrical vectors.

14. The method of claim 13, wherein generating cardiac improvement information for each pacing configuration comprises generating dyssynchrony information for each pacing configuration by monitoring heart function using at least one of a plurality of surface electrodes during pacing and cardiac imaging apparatus during pacing.

15. The method of claim 14, wherein the dyssynchrony information comprises a dyssynchrony improvement value for each pacing configuration, wherein the dyssynchrony improvement value is generated by comparing baseline dyssynchrony to paced dyssynchrony during pacing using each pacing configuration.

16. The method of claim 14, wherein selecting one or more pacing configurations based on the cardiac improvement information comprises:
   defining a threshold value based on the dyssynchrony information; and
   selecting one or more pacing configurations having a dyssynchrony improvement value greater than the threshold value.

17. The method of claim 13, wherein the electrode apparatus further comprises at least one lead, wherein the plurality of electrodes are coupled to the at least one lead.

18. The method of claim 13, wherein a common anode is used when delivering pacing therapy using each pacing configuration of the plurality of different pacing configurations to be used to generate cardiac improvement information.

19. The method of claim 13, wherein the method further comprises delivering pacing therapy using at least one pacing configuration that uses two or more electrodes of the plurality of electrodes per cardiac cycle if the cardiac improvement information generated for each pacing configuration that uses one electrode of the plurality of electrodes does not meet a threshold criteria.

20. The method of claim 13, wherein generating longevity information for each electrical vector of the plurality of electrical vectors comprises determining at least one of a capture threshold for each electrical vector and an impedance value for each electrical vector.

21. The method of claim 13, wherein the method further comprises:
   determining whether each electrical vector stimulates the phrenic nerve; and
   identifying the one or more optimal electrical vectors of the plurality of electrical vectors based on an absence of phrenic nerve stimulation.

22. The method of claim 13, wherein identifying the one or more optimal electrical vectors of the plurality of electrical vectors based on the longevity information comprises identifying the electrical vector having at least one of the greatest longevity, lowest capture threshold, and smallest impedance.

23. The method of claim 13, wherein the method further comprises identifying, on the graphical user interface, the identified one or more optimal electrical vectors on a graphical depiction of at least a portion of anatomy of the patient's heart.

24. The method of claim 13, wherein the method further comprises:
   determining one or more candidate regions proximate the patient's heart for implantation of an implantable electrode based on the identified one or more optimal electrical vectors; and
   identifying, on the graphical user interface, the one or more candidate site regions on a graphical depiction of at least a portion of anatomy of the patient's heart for implantation of the implantable electrode.

25. A system for use in cardiac therapy comprising:
   means for deliver pacing therapy using each pacing configuration of a plurality of different pacing configurations, wherein each pacing configuration uses one or more electrodes of a plurality of electrodes to deliver electrical pacing stimulation;
   computing means for generating cardiac improvement information for each pacing configuration, wherein the cardiac improvement information is representative of a change in mechanical and/or electrical cardiac functionality resulting from pacing delivered using each pacing configuration, for selecting one or more pacing configurations of the plurality of different pacing configurations that each used one or more electrodes of the plurality of electrodes to deliver pacing stimulation based on the cardiac improvement information, wherein each of the one or more selected pacing configurations that used one or more electrodes of the plurality of electrodes to deliver pacing stimulation are usable with one or more other electrodes to define a plurality of electrical vectors, wherein each of the plurality of electrical vectors are defined by at least one of the one or more electrodes used by the one or more selected pacing configurations to deliver pacing stimulation and at least one of the one or more other electrodes, for generating longevity information for each electrical vector of the plurality of electrical vectors, wherein the longevity information comprises at least energy expenditure expressed in actual or predicted battery longevity, and for identifying one or more optimal electrical vectors of the plurality of electrical vectors based on the longevity information; and display means for providing a graphical user interface information for use in assisting a user in at least one of assessing a patient's cardiac health, evaluating and adjusting cardiac therapy delivered to a patient, and navigating at least one implantable electrode to a region of the patient's heart, wherein the information comprises the identified one or more optimal electrical vectors.

\* \* \* \* \*